US006800661B1

(12) United States Patent
Rinehart et al.

(10) Patent No.: US 6,800,661 B1
(45) Date of Patent: Oct. 5, 2004

(54) SPISULOSINE COMPOUNDS

(75) Inventors: Kenneth L. Rinehart, Urbana, IL (US); Robert A. Warwick, Urbana, IL (US); Jesus Avila, Madrid (ES); Nancy L. Fregeau Gallagher, Wheeling, IL (US); Dolores Garcia Gravalos, Madrid (ES); Glynn T. Faircloth, Cambridge, MA (US)

(73) Assignee: Board of Trustees of the University of Illinois, Champaign, IL (US)

( * ) Notice: Subject to any disclaimer, the term of this patent is extended or adjusted under 35 U.S.C. 154(b) by 0 days.

(21) Appl. No.: 09/386,724

(22) Filed: Aug. 31, 1999

Related U.S. Application Data

(63) Continuation-in-part of application No. 09/058,456, filed on Apr. 10, 1998, now Pat. No. 6,107,520
(60) Provisional application No. 60/043,326, filed on Apr. 15, 1997, and provisional application No. 60/043,599, filed on Apr. 15, 1997.

(51) Int. Cl.$^7$ .............................................. A61V 31/13
(52) U.S. Cl. ...................................... 514/667; 514/669
(58) Field of Search ................................ 514/669, 667

(56) References Cited

U.S. PATENT DOCUMENTS

| 4,816,450 A | 3/1989 | Bell et al. ....................... 514/25 |
| 5,190,876 A | 3/1993 | Merrill, Jr. et al. .......... 435/240 |

FOREIGN PATENT DOCUMENTS

| EP | 0 381 514 A2 | 8/1990 | .......... A61K/31/13 |
| EP | 0 821 068 A2 | 1/1998 | .......... C12P/13/02 |
| WO | WO 96/18404 | 6/1996 | .......... A61K/31/70 |

OTHER PUBLICATIONS

See–Lasley et al., Manual of Oncology therapeutics, The C. V. Mosgy Co., St. Louis, 1981, pp446–447.*

H. Sun et al., "Weinbersterol Disulfates A and B, Antiviral Steriod Sulfates from the Sponge *Petrosia Weinbergi*", *Tetrahedron*, vol. 47, No. 7, pp. 1185–1190 (1991).

S. Sakemi et al., "Antitumor Cyclic Peroxides from the Sponge *Plakortis Lita*", *Tetrahedron*, vol. 43, No. 1, pp. 263–268 (1987).

S. Sakemi et al., "Isolation and Structure Elucidation of Onnamide A. a New Bioactive Metabolite of a Marine Sponge, *Theonella sp.*", *J. Am. Chem. Soc.*, vol. 110, pp. 4851–4853 (1988).

M. Murata et al., "Structures and Configurations of Ciguatoxin from the Moray Eel *Gymnothorax javanicus* and Its Likely Precursor from the Dinoflagellate *Gambierdiscus toxicus*", *J. Am. Chem. Soc.*, vol. 112, pp. 4380–4386 (1990).

M. Kernan et al., "Macrocyclic Antifungal Metabolites from the Spanish Dancer Nudibranch Hexabranchus *sanguineus* andd Sponges of the Genus *Halichondria*", *J. Org. Chem.*, vol. 53, pp. 5014–5020 (1988).

G. Pettit et al., "Antneoplastic Agents. 224 Isolation and Structure of neristatin $1^{1a}$", *J. Am. Chem. Soc.*, vol. 113, No. 17, pp. 6693–6695 (1991).

D. Schaufelberger et al., "Revised Structure of Byrostatin 3 and Isolation of the Bryostatin 3 26–Ketone from *Bugula neritina*", *J. Org. Chem.*, vol. 56, pp. 2895–2900 (1991).

W. Murayama et al., "A New Centrifugal Counter–Current Chromatograph and Its Application", *Journal of Chromatography*, vol. 239, pp. 643–649 (1982).

D. Martin et al., "Countercurrent Chromatography for Drug Discovery and Development", *CCC for Drug Discovery and Development*, Chapter Nine, pp. 565–581.

S. Kohmoto et al., "Isospongiadiol, a Cytotoxic and Antiviral Diterpene from a Caribbean Deep Water Marine Sponge, *Spongia sp.*", *Chemistry Letter*, pp. 1687–1690 (1987).

G. Pettit et al., "Isolation and Structure of Bryostatins 14 and $15^1$", *Tetrahedron*, vol. 47, No. 22, pp. 3601–3610 (1991).

R. Bruening et al., "Isolation of Tunichrome B–1, A Reducing Blood Pigment of the Sea Squirt, *Ascidia Nigra$^1$*", *Journal of Natural Products*, vol. 49, No. 2, pp. 193–204 (1986).

M. Reetz et al., "Sterioselective Synthesis of β–Amino Alcohols from Optically Active a–Amino Acids", *Angew. Chem. Int. Ed. Eng.*, vol., 26, No. 11, pp. 1141–1143 (1987).

Prostenik et al., "Application of the Asymmetric Synthesis in the Determination of the Configuration of Amino Alcohols and Diamines with Two Adjacent Asymmetric Carbon Atoms", *Croatica Chemica Acta*, vol. 29, pp. 393–402 (1957).

B. Ravi et al., "Recent Research in Marine Natural Products: The Puupehenones", *Pure & Appl. Chem.*, vol. 51, pp. 1893–1900.

A. Stierle et al., "A Marine Micrococcus Produces Metabolites Ascribed to the Sponge *Tedania ignis*", *Experientia*, vol. 44, pp. 1021 (1988).

F. Schmitz et al., "Metabolites from the Marine Sponge *Tedania ignis*. A New Atisanediol and Several Known Diketopiperazines$^1$", *J. Org. Chem.*, vol. 48, pp. 3941–3945 (1983).

R. Dillman et al., "An Unusual Sulfur–Containing Diketopiperazine from the Bermudian Sponge *Tedania Ignis$^1$*", *Journal of Natural Products*, vol. 54, No. 4, pp. 1159–1161 (1991).

(List continued on next page.)

*Primary Examiner*—Rebecca Cook
(74) *Attorney, Agent, or Firm*—Kenneth Sonnenfeld; Michael Willis; Morgan & Finnegan, L.L.P.

(57) ABSTRACT

Investigation of the activity of extracts of the clam *Spisula polynyma* has led to antitumour long-chain, straight-chain alkane or alkene compounds which have a 2-amino group and a 3-hydroxy group.

9 Claims, 6 Drawing Sheets

OTHER PUBLICATIONS

A. Stierle et al., "Maculosin, a host–speciific phytotoxin for spotted knapweed from *Alternaria alternata*", *Proc. Natl. Acad. Sci USA*, vol. 85, pp. 8008–8011 (1988).

A. Stierle et al., "Benzothiazoles From a Putative Bacterial Symbiont of the Marine Sponge *Tedania ignis*[1]", *Tetrahedron Letters*, vol. 32, No. 37, pp. 4847–4848 (1991).

M. Raub et al., "Clavepictines A and B: Cytotoxic Quinolizines From the Tunicate *Clavelina picta*[1]", *J. Am. Chem. Soc.*, vol. 113, pp. 3178–3180 (1991).

S. Sakemi et al., "Xestamines A, and B and C, Three New Long–Chain Methoxylamine Pyridines from the Sponge Xestopongia Weidenmayeri", *Journal of Natural Products*, vol. 53, No. 4, pp. 995–999 (1990).

D. Steirle et al., "Antimicrobial N–Methylpyridinium Salts Related to the Xestamines From the Caribbean Sponge *Calyx Podatypa*", *Journal of Natural Products*, vol. 54, No. 4, pp. 1134–1136 (1991).

S. Kohmoto et al., "1,1–Dimethyl–5–6–dihydroxyindolinium chloride from a deep water marine spong, *Dercitus sp.*", *Experietia*, vol. 44, pp. 85–86.

H. Sun, et al., "A Brominated (Aminoimidazolinyl)indole from the Sponge *Discodermia polydiscus*", *Journal Org. Chem.* vol. 56, pp. 4307–4308 (1991).

R. Sakai et al., "Manzamine B and C, Two Novel Alkaloids from the Sponge *Haliclomasp.*", *Tetrahedron Letters*, vol. 28, No. 45, pp. 5493–5496 (1987).

S. Bobzin et al., Aromatic Alkaloids from the Marine Sponge *Chelonaplysilla sp.*, *J. Org. Chem.*, vol. 56, pp. 4403–4407 (1991).

S. Sakemi et al., "Nortopsentins A, B, and C. Cytotoxic and Antifungal Imidazolediylbis[indoles] from the Sponge *Spongosorites ruetzleri*", *J. Org. Chem.*, vol. 56, pp. 4304–4307 (1991).

P. Keifer et al., "Bioactive Bromopyrrole Metabolites from the Caribbean Sponge *Angelas conifera*", *J. Org. Chem.*, vol. 56, pp. 2965–2975 (1991).

F. Schmitz et al., "Biologically active compounds from marine organisms", *Pure & Appl. Chem.*, vol. 62, No. 7, pp. 1393–1396 (1990).

D. Schaufelberger et al., "Separation of Pyrroloimidazoles from Indo–Pacific Marine Sponges by High–Speed Countercurrent Distribution", *Journal of Liquid Chromatography*, pp. 1909–1917 (1989).

G. Pettit et al., "Antineoplastic agents. 168. Isolation and structure of axinonydantoin[1]", *Can. J. Chem.*, vol. 68, pp. 1621–1624 (1990).

F. Schmitz et al., "Cytotoxic Aromatic Alkaloids from the Ascidian *Amphicarpa meridiana* and *Leptoclinides* sp.: Meridine and 11–Hydroxyascididemin", *J. Org. Chem.*, vol. 56, pp. 804–808 (1991).

G. Gunawardana et al., "Dercitin, a New Biologically Active Acridine Alkaloid from a Deep Water Marine Sponge, *Dercitus sp.*", *J. Am. Chem. Soc.*, vol. 110, pp. 4856–4848 (1988).

G. Gunawardana et al., "Pyridoacridine Alkaloids from Deep–Water Marine Sponges of the Family Pachastrellidae: Structure Revision of Dercitin and Related Compounds and Correlation with the Kuanoniamines", *J. Org. Chem.*, vol. 57, pp. 1523–1526 (1992).

G. Gunawardana et al., "New Cytotoxic Acridine Alkaloids from Two Deep Water Marine Sponges of the Family *Pachastrellidae*", *Tetrahedron Letters*, vol. 30, No. 33, pp. 433359–433362 (1992).

S. Sakemi et al., "Batzellines A, B, C, Novel Pyrroloquinoline Alkaloids From the Sponge *Batzella Sp.*", *Tetrahedron Letters*, vol. 30, No. 19, pp. 2517–2520 (1989).

H. Sun et al., "Isobatzellines A, B, C, and D. Cytotoxic and Antifungal Pyrroloquinoline Alkaloids from the Marine Sponge *Batzella sp.*", *J. Org. Chem.*, vol. 55, pp. 4964–4966 (1990).

G. Kalaus et al., "Synthesis of Vinca Alkaloids and Related Compounds. 37[1]. Some New Reactions of (±)–C–Norquebrachamine and Its Derivatives", *J. ORg. Chem.*, vol. 53, pp. 42–45 (1988).

E. Jares–Erijman et al., "Crambescidins: New Antiviral and Cytotoxic Compounds from the Sponge *Crambe crambe*[1]", *J. Org. Chem.*, vol. 56, pp. 5712–5715 (1991).

Y. Kashman, et al., "Ptilomycalin A: A Novel Polycyclic Guanidine Alkaloid of Marine Origin", *J. Am. Chem. Soc.*, vol. 111, pp. 8925–8926 (1989).

R. Berlinck et al., "Two new guanidine alkaloids from the Mediterranean sponge Crambe crambe", *Tetrahedron Letter*, vol. 31, No. 45, pp. 6531–6534 (1990).

K. Rinehart et al., "Ecteinascidins 729, 743, 745, 759A, 759B, and 770: Potent Antitumor Agents from the Caribbean Tunicate *Ecteinascidia turbinata*[1]", *J. Org. Chem.*, vol. 55, pp. 4512–4515 (1990).

A. Wright, et al., "Antitumor Tetrahydroisoquinolline Alkaloids from the Colonial Ascidian *Ecteiinascidia turbinata*", *J. Org. Chem.*, vol. 55, pp. 4508–4512 (1990).

R. Brusca and G. Brusca, *Invertebrates*, Sinauer Associates, Sunderland, MA, (1990), pp. 706–709.

B. Palameta et al., "Chromatography of the Lipide Bases on Paper Impregnated with Silicic Acid", *Croatica Chemica Acta*, vol. 33, pp. 133–135 (1961).

Y. Kawano et al., "Isolation and Structure of Six New Cerebrosides", *Biologically Active Glycosides from Asteroidea*, XIII, pp. 19–24.

N. Gulavita et al., "Two Epimeric Aliphatic Amino Alcohols from a Sponge, Xestopongia sp.", *J. Org. Chem.*, vol. 54, No. 2, pp. 367–369 (1989).

C. Jimenez et al., "Novel Marine Sponge Amino Acids, 10. [1] Xestoaminols from Xestospongia Sp.", *Journal of Natural Products*, vol. 53, No. 4, pp. 978–982 (1990).

K. Mori et al., "Synthesis and Absolute Configuration of the Two Epimeric Aliphatic Amino Alcoholss [(5E, 7E)–2–Amino–5–7–tetradecadien–3–ols] Isolated from a Sponge, *Xestrospongia sp.*", *Synthesis if Sphingosine Relative*, XIII, pp. 131–137.

J. Osby et al., "An Exceptionally Mild Deprotection of Phthalimides", *Tetrahedron LettersI*, vol. 25, No. 20, pp. 2093–2096 (1984).

W. Stoffel, "Sphingolids" (1971), pp. 57–82.

A. Merrill et al., "Structural Requirement for Long–Chain (Sphingoid) Based Inhibition of Protein Kinase C in Vitro and for the Cellular Effects of These Compounds", *Biochemistry*, vol. 28, pp. 3138–3145 (1989).

Y. Hannun et al., "Functions of Sphingolipids and Sphingolipid Breakdown Products in Cellular Regulation", *Science*, vol. 243, pp. 500–507.

A. Merrill, "Cell Regulation by Sphingosine and More Complex Sphingolipids[1]", *Journal of Bioenergentics and Biomembranes*, vol. 23, No. 1, pp. 83–104 (1991).

J. Witten et al., "Structure of Two Cockroach Neuropeptides Assigned by Fast Atom Bombardment Mass Spectrometry", *Biochemical and Biophysical Research Communication*, vol. 124, No. 2, pp. 350–358 (1984).

E. Hermann et al., "The Detection, Assay and Evaluation of Antiviral Drugs", *Progr. med. Virol.*, vol. 3, pp. 158–192 (1961).

S. Grode et al., "Ceramides from the Sponge *Dysidea etheria[1]*", *Lipids,* vol. 18, No. 12, pp. 889–893 (1983).

*Chem. Abs.,* 1991, 114, 214413b.

D.J. Faulkner, "Marine Natural Products", *Nat. Prod. Rep.,* vol. 8, pp. 97–147 (1991).

M.H.G. Munro, et al., "The Search for Antiviral and Anticancer Compounds from Marine Organisms", *Bioorganic Marine Chemistry,* vol. 1, pp. 93–176 (1987).

Barry C. Smith et al., "Phytoplankton Pigments Accumulated by the Artic Surfclam", *Journal of Shellfish Research,* vol. 11, No. 2, pp. 479–483 (1992).

Nancy Louise Fregeau, Ph.D. Thesis entitled "Biologically Active Compounds from a Clam and a Tunuicate" submitted in partial fulfillment of the requirements for the degree of Doctor of Philosophy in chemistry in the Graduate College of the University of Illinois at Urbana–Champaign, 1992. First released to the public by the University—Apr. 14, 1998.

\* cited by examiner

1A

1D

1B

1E

1C

1F

SPISULOSINE COMPOUNDS

CROSS-REFERENCE TO RELATED APPLICATION

This application is a continuation-in-part of application Ser. No. 09/058,456, filed Apr. 10, 1998, allowed as U.S. Pat. No. 6,107,520, which claims the benefit of U.S. Provisional Application Ser. No. 60/043,326 filed Apr. 15, 1997, and U.S. Provisional Application Ser. No. 60/043,599, the disclosures of which are hereby incorporated herein by reference.

FIELD OF THE INVENTION

The present invention relates to pharmaceutical compositions of spisulosine compounds. It further relates to the treatment of tumors, and provides new cytotoxic compounds and pharmaceutical compositions for use against tumors. In one aspect, the invention relates to antitumor compounds from marine organisms.

BACKGROUND OF THE INVENTION

There has been considerable interest in isolating bioactive compounds from marine organisms. Typical procedures involve in vitro screening programs to test crude extracts for antimicrobial, antiviral, and cytotoxic activities. Illustrative examples of known bioactive compounds from marine sources include bryostatins, ecteinascidins and furthermore didemnins where didemnin B, also now known as aplidine, is the first marine natural product in clinical testing.

SUMMARY OF THE INVENTION

The present invention provides new pharmaceutical compositions containing a long-chain, straight-chain alkane or alkene compound which has a 2-amino group and a 3-hydroxy group, together with a pharmaceutically acceptable carrier. Typically the compound is a 2-amino-3-hydroxyalkane or a 2-amino-1,3-dihydroxyalkene. Preferably the compound is a substituted $C_{10}$–$C_{24}$ alkane or alkene. The compound is preferably a substituted alkane, more preferably a substituted $C_{18}$–$C_{20}$ alkane, and most preferably a 2-amino-3-hydroxy $C_{18}$ alkane. The substituted alkene is preferably a substituted mono- or di-alkene, more preferably a substituted $C_{18}$–$C_{20}$ alkene. In one embodiment, the compounds have the partial stereochemistry:

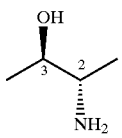

In particular, the present invention provides compositions which contain bioactive sphingoid-type bases, spisulosines 285, 299 and 313 (1–3), sphingosine (also referred to as 4-sphingenine or octadeca-4-sphingenine, 4) and two related compounds, nonadeca-4-sphingenine (a one carbon longer homologue, 5) and sphinga-4,10-diene (a dehydrosphingosine derivative, 6).

Thus, the preferred compositions contain one or more of the following preferred compounds:

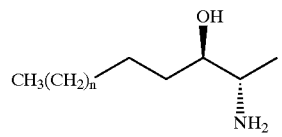

spisulosine 285 (1), n=12; spisulosine 299 (2), n=13; spisulosine 313 (3), n=14

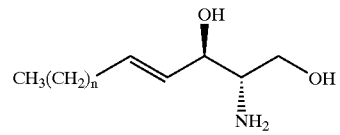

as well as sphingosine (4), n=12 and nonadeca-4-sphingenine (5), n=13; and

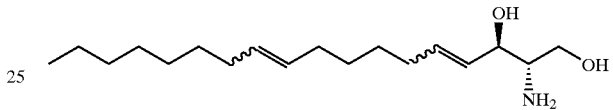

sphinga-4,10-diene (6).

The preferred compound, spisulosine 285, is known in the literature. Compound 1 and the syn diastereoisomer, were first synthesized by Croatian researchers in the determination of absolute configurations of lipid bases with two or more asymmetric carbon atoms, see Prostenik, M., Alaupovic, P. *Croat. Chem. Acta.* 1957, 29, 393.

It is believed that the other compounds in the compositions of this invention are new compounds.

Compounds 1–3 show unique cytotoxicity against L1210 murine lymphocytic leukemia cells. In a number of the L1210 assays, a distinct morphological alteration was observed. This effect was also described in our earlier U.S. Provisional Patent Application Serial No. 60/043,326. We make no patent claim in this patent application to the effect itself on L1210, and indeed there is now some preliminary data that suggests that the compounds such as spisulosine 285 might lack activity against leukemia tumors.

A synthetic sample of 1 was assayed against L1210 leukemia cells and showed both cytotoxicity and morphological alteration, pointed cell activity.

| L1210 Inhibition and pointed cell activity | | |
|---|---|---|
| Concentration | % cytotoxicity | % pointed cells[a] |
| 0.5 μg/ml | 100 | 97 |
| 0.25 μg/ml | 99 | 100 |
| 0.1 μg/ml | 99 | 62 |
| 0.05 μg/ml | 96 | 71 |
| 0.025 μg/ml | 90 | 21 |
| 0.01 μg/ml | 45 | 1 |

[a]Percent pointed cells are a percent of the living cells.

Spisulosine 285 (1) is also active against other tumor cell lines in vitro, including P-388 (0.01 mg/ml); A-549 (0.05 mg/ml); HT-29 (0.05 mg/ml) and MEL-28 (0.05 mg/ml).

In a particularly preferred embodiment, the present invention relates to use of spisulosine 285, and related compounds, in the treatment of all types of cancer, such as breast cancers, prostate, bladder, pancreas, lung, esophagus, larynx, liver, colon, thyroid, melanoma, kidney, testicular, leukemia, ovarian, gastro-intestinal, hepatocellular carcinoma and vascular endothelial cancer. Other forms of cancer are well known to the person skilled in the art. It is preferred that the use of spisulosine 285, and related compounds is against solid tumors, with use against slow proliferating tumors such as prostate, lung, liver, kidney, endocrine gland and vascular endothelial cancer particularly preferred. In one aspect, the compositions are for use in therapy directed at the vascular endothelium for control of tissue and tumor vascularisation.

The present invention is directed to bioactive compounds that have been found to possess specific antitumor activities and as such they will be useful as medicinal agents in mammals, particularly in humans. Thus, another aspect of the present invention concerns pharmaceutical compositions containing the active compounds identified herein and methods of treatment employing such pharmaceutical compositions.

The active compounds of the present invention exhibit antitumor activity. Thus, the present invention also provides a method of treating any mammal affected by a malignant tumor sensitive to these compounds, which comprises administering to the affected individual a therapeutically effective amount of an active compound or mixture of compounds, or pharmaceutical compositions thereof. The present invention also relates to pharmaceutical preparations, which contain as active ingredient one or more of the compounds of this invention, as well as the processes for its preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Administration of the composition of the present invention may be by any suitable method, such as intravenous infusion, oral preparations, intraperitoneal and intravenous administration. Intravenous delivery may be carried out over any suitable time period, such as 1 to 4 hours or even longer if required, at suitable intervals of say 2 to 4 weeks. Pharmaceutical compositions containing spisulosine may be delivered by liposome or nanosphere encapsulation, in sustained release formulations or by other standard delivery means.

The correct dosage of a pharmaceutical composition comprising the compounds of this invention will vary according to the particular formulation, the mode of application, and the particular situs, host and bacteria or tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds may be provided in the pharmaceutical compositions of this invention in the form of a prodrug or precursor, which upon administration converts or is metabolized to the active compound.

The compositions of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);
b) antimetabolite drugs such as 5-fluorouracil, cytarabine, gemcitabine, purine analogues such as pentostatin, methotrexate);
c) alkylating agents such as nitrogen mustards (such as cyclophosphamide or ifosphamide);
d) drugs which target DNA such as the antracycline drugs adriamycin, doxorubicin, pharmorubicin or epirubicin;
e) drugs which target topoisomerases such as etoposide;
f) hormones and hormone agonists or antagonists such as estrogens, antiestrogens (tamoxifen and related compounds) and androgens, flutamide, leuprorelin, goserelin, cyprotrone or octreotide;
g) drugs which target signal transduction in tumour cells including antibody derivatives such as herceptin;
h) alkylating drugs such as platinum drugs (cis-platin, carboplatin, oxaliplatin, paraplatin) or nitrosoureas;
i) drugs potentially affecting metastasis of tumours such as matrix metalloproteinase inhibitors;
j) gene therapy and antisense agents;
k) antibody therapeutics; and
l) other bioactive compounds of marine origin, notably the ecteinascidins such as ET-743, or the didemnins such as aplidine.

The present invention also extends to the compounds for use in a method of treatment, and to the use of the compounds in the preparation of a composition for treatment of cancer.

Spisulosine 285 has an effect upon cell morphology. Vero cells treated with spisulosine 285 had a reduced microfilament structure, as assessed by staining of the spisulosine-treated cells with phalloidin, which stains actin in the microfilaments. Spisulosine 285 also affects the distribution of the small GTP binding protein Rho, although this effect may be reduced or eliminated by pre-treatment with the Rho-activator LPA (Mackay and Hall, *J. Biol. Chem.*, 273, 20685–20688, 1998).

Without wishing to be constrained by theory, we believe that the mechanism of action of spisulosine 285 may involve modulation of the action of the small GTP binding protein Rho, possibly via an effect on LPA activation. Rho is known to be involved in the formation of stress fibers (Hall, A., *Science* 279, 509–514, 1998), and has a role in controlling cell adhesion and motility through reorganization of the actin cytoskeleton (Itoh, et al, *Nature Medicine*, Vol 5, No. 2, (reducing) the levels of microfilaments in the cell, via an (inhibitory) effect on Rho, spisulosine 285 may serve to limit the development of cancer via an effect on the cell cytoskeleton. It is also known that Rho triggers progression of the G1 phase of the cell cycle. As such, modulation of Rho may also prevent cellular transformation by stopping cell cycle progression. Therefore, the present invention also relates to the use of spisulosine compounds in the preparation of a medicament for the treatment of cancer, wherein the spisulosine compound acts to alter Rho protein activity.

LPA, an activator of Rho, can help prevent the effect of spisulosine compounds on microfilament formation. While the specific target of spisulosine 285 is not known, the observed reduction of actin microfilaments in cells treated with spisulosine 285 and the lipid structure of spisulosine 285 suggest that spisulosine compounds may serve as an antagonist for the LPA receptor, preventing LPA interacting with its receptor to activate Rho to produce the microfilaments.

The preferred compounds of this invention were initially isolated from *Spisula polynyma*. *Spisula polynyma* is an edible clam, which is also known as the Stimpson surf clam or the Atlantic surf clam. It belongs to the subfamily Mactrinae, family Mactridae, superfamily Mactroidea, order Veneroida, subclass Heterodonta, class Bivalvia, phylum Mollusca. *Spisula polynyma* was originally found off the coast of Japan, where it is called hokkigai and processed for sushi. It has now migrated through the Bering Strait, down past Greenland and Newfoundland, into the Atlantic ocean. The clam has a grey-white shell, 7–10 cm long. It is mainly off-white, except for the tongue which is purple in the living clam, but turns bright red after cooking.

Thus, the present invention provides active extracts of the clam *Spisula polynyma*. One embodiment of the present invention is directed to novel compounds isolated from the clam *Spisula polynyma*, and the use of all of the cytotoxic compounds isolated therefrom as antitumor compounds.

To test for biological activity, one clam was homogenized in 3:1 methanol/toluene. A solution of sodium chloride was added to this crude extract, causing it to separate into a toluene and an aqueous layer. The latter was further extracted with toluene, dichloromethane, ethyl acetate and 1-butanol. These extracts were all assayed against L1210 cells, where significant cytotoxicity was observed for the initial crude, toluene and dichloromethane extracts and less activity in the other three fractions.

mg/6.35-mm disk), but no activity was observed. No antimicrobial activity was observed for these extracts against *Penicillium melinii* (formerly *P. atrovenetum*) and *Micrococcus luteus* (formerly *Sarcina lutea*, both at 500 mg/ 12.7-mm-disk). Later, other more purified extracts were assayed against *Bacillus subtilis, Saccharomyces cereuisiae*, and *Escherichia coli* with no bioactivity observed.

Synthetic methods are also available for the preparation of spisulosine compounds, particularly spisulosines 285 (1), 299 (2) and 313 (3).

The preferred synthetic route is based upon the previous addition of organometallics to N,N-dibenzylamino aldehydes to yield β-amino alcohols with high stereoselectivity. See, Andres et al., *Org. Chem.* 1996, 61, 4210 and Reetz et al., *Angew Chem. Int. Ed. Engl.,* 1987, 26, 1141. The non-chelation controlled addition of Grignard reagents or organolithium compounds produces the anti-diastereomer and the chelation controlled addition of organozinc preferentially gives the syn-diastereomer.

Scheme I illustrates this preferred synthetic process for the formation of Compound 1:

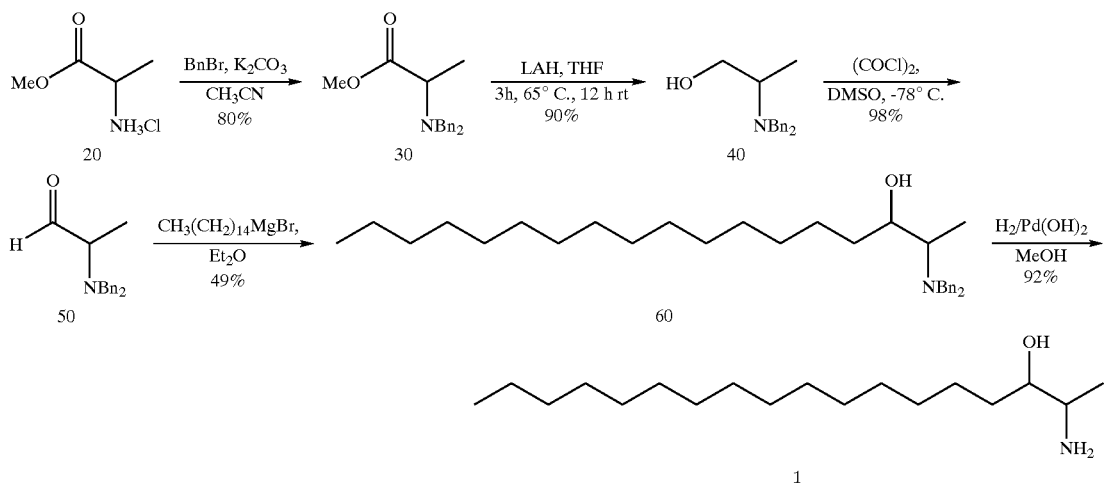

As described in Scheme 1, the β-amino aldehyde 50 can be prepared from L-alanine methyl ester by first dibenzylation of the amino group with benzyl bromide and potassium carbonate followed by lithium aluminum hydride reduction to the N,N-dibenzylamino alcohol 40. The Swern oxidation of 40 gives 50 in high yield and can be used without further purification to avoid decomposition. Addition of the Grignard reagent to 50 gives the anti-diastereomer 60 with high selectivity. The compound, 60, can be easily purified, for example by flash chromatography and HPLC. The deprotection of 60 by hydrogenolysis on Pearlman's catalyst gives 1 in high yield and a good overall yield. Compounds 2 and 3 may be prepared simply by increasing the chain length of the Grignard reagent, and the remaining compounds of the present invention may also be prepared by appropriate choice of the Grignard reagent.

L1210 Cytotoxicity of Crude Extracts of *Spisula polynyma*[a,b]

| Extract | Concentration (μg/ml) | | | | | |
|---|---|---|---|---|---|---|
| | 250 | 125 | 50 | 25 | 12.5 | 5 |
| Crude | 98* | 98* | 92 | 25 | 0 | 0 |
| Toluene | 100* | 100* | 100* | 25 | 13 | 13 |
| CH$_2$Cl$_2$ | 100* | 100* | 100* | 91 | 20 | 13 |
| EtOAc | 98* | 98* | 92* | 0 | 0 | 0 |
| 1-BuOH | 83 | 33 | 0 | 0 | 0 | 0 |
| Aqueous[c] | 94 | 75 | 0 | 0 | 0 | 0 |

Footnotes:
[a]cytotoxicity reported as % inhibition of growth;
[b]entries marked with * showed pointed cell activity;
[c]the aqueous extract was assayed at 700, 350, 140 70, 35 and 14 mg/ml.

These extracts were also assayed against Herpes simplex virus Type 1 (HSV-1) and CV-1 monkey kidney cells (at 100

BRIEF DESCRIPTION OF THE DRAWINGS

FIG. 1A represents a normal cell; FIG. 1B represents a typical pointed cell: FIG. 1C represents an atypical pointed cell; FIG. 1D represents a cell with more than two points; FIG. 1E represents a bulged cell; and FIG. 1F represents a combined bulged and pointed cell.

DETAILED DESCRIPTION OF THE INVENTION

Figure 1:
FIGS. 1A, 1B, 1C, 1D, 1E and 1F are illustrations of the cell morphologies observed in the L12 10 assays of *Spisula polynyma* extracts.
Figure 1:
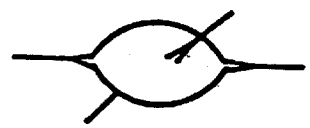
Figure 1:
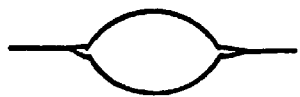
Figure 1:
Figure 1:
Figure 1:

Referring to FIG. 1, in the L1210 assay some of the cells changed from being spherical (FIG. 1A) to ovoid with long points approximately 180° C. apart (FIG. 1B). Several other forms have also been observed in assays of these extracts, including cells with points not 180° C. apart (FIG. 1C), cells with more than two points (FIG. 1D), cells with a bulge (FIG. 1E) and cells with a bulge replacing one of the points (FIG. 1F). However, the form with two sharp, opposing points was by far the predominant and characteristic one observed. This type of morphological change had not previously been observed during the screening of over 1000 marine extracts.

Isolation of Spisulosines 285, 299, and 313

For this invention, *Spisula polynyma* were collected, at a depth of −110 feet, from a clam bed on the eastern edge of Stellwagon bank which is located off the coast of New England, stretching from near Gloucester, Mass., north to Maine. They were shipped live by the New England Clam Corporation (formerly New Dawn Seafoods, Inc.) and then immediately frozen.

Figure 2:
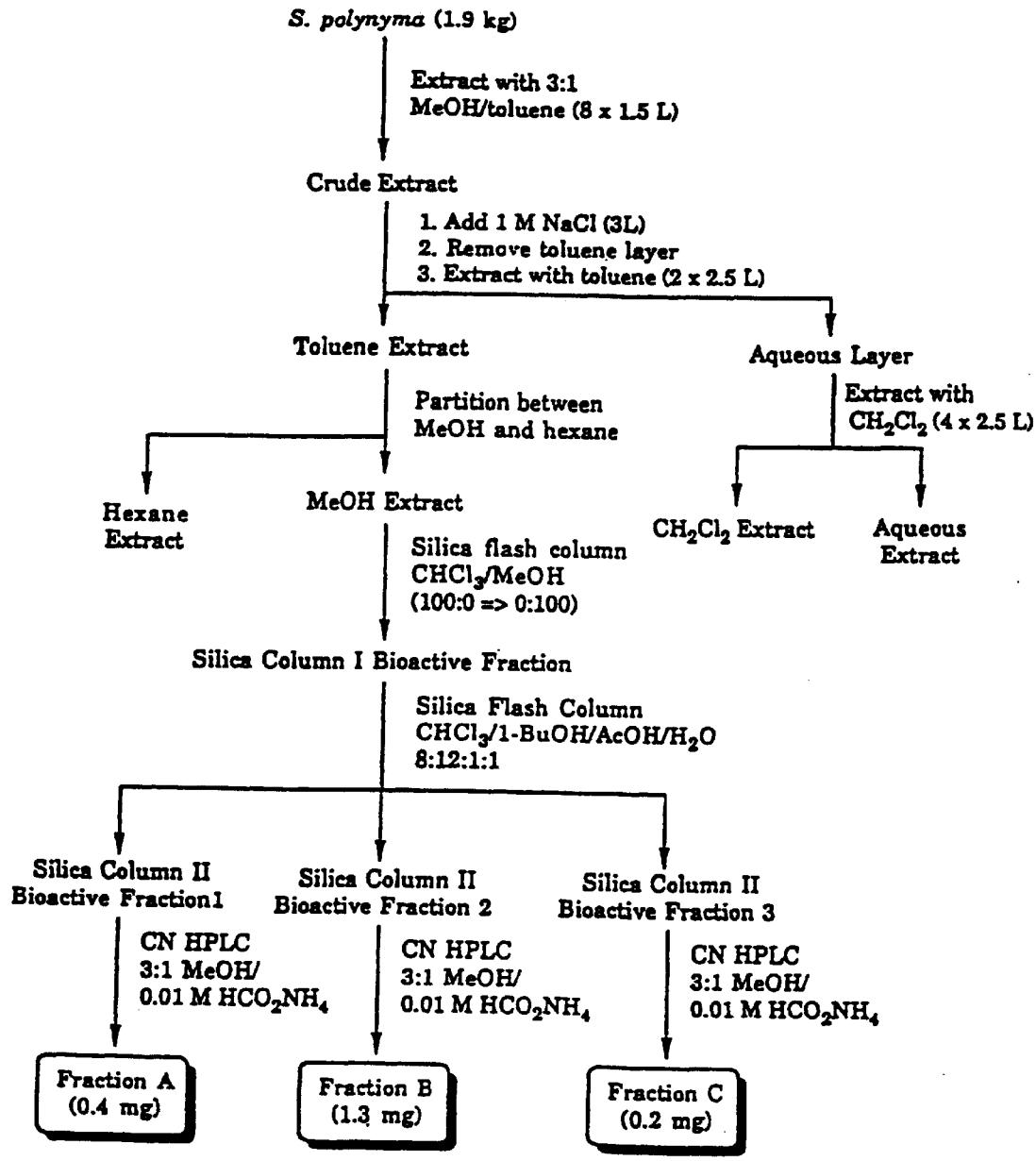
FIG. 2 illustrates the scheme used to separate the compounds described herein from extracts of the clam *Spisula polynyma*.

A purification scheme similar to the extraction procedure described above for the original testing of the bioactivity was employed. First 35 clams were thawed and the shells removed to give 1.9 kg (wet wt). These were allowed to stand in 3:1 methanol/toluene and filtered after several hours. This step was repeated followed by homogenization and extensive extraction with this same solvent to give a crude extract. To this was added a 1 M sodium chloride solution which caused the extract to separate into two layers. The lower aqueous layer was further extracted with toluene and the toluene layers combined. The resulting aqueous layer was then extracted with dichloromethane as shown in FIG. 2.

The toluene extract was partitioned between methanol and hexane. The cytotoxicity and cellular alteration were observed almost exclusively in the methanol fraction. The methanol extract thus obtained was applied to a silica flash column, eluting with a chloroform/methanol step gradient (100:0, 99: 1. 95:5, 90:10, 85:15, 80:20, 70:30, 50:50, 0:100). The main cytotoxic and pointed-cell-forming activity eluted off the column very late, although earlier fractions did show some cytotoxicity, but no pointed cells. This late eluting was further purified by flash silica chromatography, using 8:12:1:1 chloroform/1-butanol/acetic acid/water. Fractions were neutralized with sodium bicarbonate before removing the solvent to prevent possible decomposition when they were concentrated in acid. This resulted in a series of three bioactive fractions.

It had been observed in earlier attempts at isolation that the bioactivity did not wash off of a cyano solid-phase extraction (SPE) column with methanol, but the cytotoxicity was found to elute with 3:1 methanol/0.01 M ammonium formate (0.5 ml/min). This was confirmed by chromatographing a small amount of a bioactive fraction on a cyano HPLC column with this same solvent system and then repeating the injection under the same conditions except replacing the ammonium formate solution with water. The chromatograms appeared identical except that a peak eluting at 15.6 min was only observed in the first.

The three bioactive fractions from the second silica column were each further purified by cyano HPLC with the same conditions used above (except 1 ml/min) to give three series of bioactive fractions. The ammonium formate was removed by passing the sample through a C-18 SPE column, washing first with water and then eluting with methanol. The main cytotoxicity and morphology-changing activity of each series (fractions A, B, and C) was found in a peak comparable to that discussed above. However the activity was spread throughout most of the fractions. Silica TLC (3:12:2:2 chloroform/1-butanol/acetic acid/water) indicated that fraction A (0.4 mg) contained one spot ($R_f$ 0.47), which was pink by ninhydrin. Fraction B (1.3 mg) showed this same spot as well as one slightly lower ($R_f$ 0.44, red by ninhydrin), while fraction C (0.2 mg) contained both of these and a third one ($R_f$ 0.34, purple by ninhydrin). All three showed good cytotoxicity and pointed-cell forming activity, with A exhibiting slightly more activity than B and significantly more than C. This indicated that the uppermost TLC spot must be from compound(s) which caused the morphological change in L1210 cells. These fractions were not purified further, but analyzed as mixtures. Quantitative bioassay results are discussed below.

An attempt was made to determine if a particular organ of *Spisula polynyma* contained most or all of the bioactivity. A live clam was anesthetized with diethyl ether and then dissected into nine parts: foot, digestive system, gonads, siphon, gills, heart, mantle, adductor muscles, and the remainder of the visceral mass (with foot, digestive system and gonads removed). These were identified by comparison to illustrations of other clams. Each organ was homogenized in 3:1 methanol/toluene and the resulting extract was then triturated with dichloromethane and methanol to remove salts. While all of the extracts showed cytotoxicity (Table), only those from the gills and the gonads exhibited strong morphology-changing activity. That from the digestive system and the remainder of the visceral mass also showed weak pointed-cell forming activity, possibly due to incomplete separation from the gonads. The lack of pointed-cell-forming activity in other organs may have resulted either from a lack of 1–3 or from a much lower concentration.

In another experiment, one foot that had been cooked for a brief period was extracted in an analogous manner. This also showed cytotoxicity, but no morphology-altering activity. However, when a larger sample of cooked material was more extensively extracted, some pointed cells were observed in the L 1210 assay. Silica TLC (3:12:2:2 chloroform/1-butanol/acetic acid/water, 100 mg) of the extracts of the digestive system and gonads showed a weak ninhydrin-positive spot at $R_f$ 0.49.

| | 250 μg/ml | | 125 μg/ml | | 50 μg/ml | |
|---|---|---|---|---|---|---|
| Organ | % Inhibition | % Pointed[a] | % Inhibition | % Pointed[a] | % Inhibition | % Pointed[a] |
| foot | 100 | 0,ad[b] | 100 | 0,ad | 93 | 0,0 |
| digestive system | 96 | 0,18 | 62 | 0,0 | 0 | 0,0 |
| gonads | nr[c] | nr | 99 | 56,100 | 90 | 32,100 |
| siphon | 100 | ad,ad | 50 | 0,0 | 0 | 0,0 |
| gills | 100 | ad,ad | 100 | 50,ad | 98 | 100,93 |
| heart | 100 | ad,ad | nr | 0,0 | 38 | 0,0 |
| mantle | 100 | 0,0 | 99 | 0,0 | 95 | 0,0 |
| adductor muscles | 100 | added | 100 | 0,0 | 95 | 0,0 |
| visceral mass | 100 | 10,ad | 100 | 2,ad | 94 | 0,0 |

-continued

| | 250 µg/ml | | 125 µg/ml | | 50 µg/ml | |
|---|---|---|---|---|---|---|
| Organ | % Inhibition | % Pointed[a] | % Inhibition | % Pointed[a] | % Inhibition | % Pointed[a] |
| cooked foot[d] | 100 | 0 | 100 | 0 | 97 | 0 |
| cooked foot[e] | 91 | 21 | 25 | 0 | 0 | 0 | footnotes:
[a]Percentage of pointed cells was measured at 58 to 82 h after the start of the assay.
[b]ad = all dead.
[c]nr = not read due to precipitated material in the assay which obscured the cells.
[d]Percentage of pointed cells measured at 72 h after the start of the assay.
[e]This sample was extracted in a similar manner to that used to obtain the crude extract of the isolation of fractions A–C. Percentage of pointed cells measured at 76 h after the start of the assay.

Several clues to the structure of the bioactive compounds could be found in the isolation procedure. The TLC spot which correlated with the activity visualized as pink or red by ninhydrin, suggesting that the compounds contained primary amines. Also, they exhibited amphiphilic character. They were originally extracted into toluene from aqueous methanol, but they then partitioned into methanol versus hexane. While they are soluble in nonpolar solvents, they require a very polar solvent (3:12:2:2 chloroform/1-butanol/acetic acid/water) to be eluted from silica.

Only fractions A and B were reasonably pure from inactive contaminants as shown by TLC. Most of the structure determination studies were carried out on fraction B because of its size relative to the others. What was immediately obvious in these spectra was a peak corresponding to a long methylene chain (1.25 ppm) and several overlapping terminal methyl groups (0.87 ppm). Other peaks were not as well defined. No peaks corresponding to aromatic protons were observed, but several peaks appeared in the alkene proton region. Several others seemed to correspond to protons attached to heteroatom-substituted carbons. The major difference between the spectra in the two different solvents was that, in $CD_3OD$, a methyl doublet (1.21 ppm) downfield of the terminal methyl groups were clearly observed, while in $CDCl_3$ this resonance appeared only as an upfield shoulder on the methylene chain peak.

An authentic sample of D-trans-erythro-sphingosine (4) was obtained from Sigma for comparison with the isolated material. The $^1$H NMR spectrum thereof was similar in many respects to that of fraction B. As expected, 4 exhibited a large peak due to the long methylene chain (1.25 ppm), a terminal methyl group (0.87 ppm) and two vinyl protons (5.75 and 5.46 ppm). Of particular note was the broadness of the resonances corresponding to protons on the heteroatom-substituted carbons (4.40, 3.66, 2.85 and 2.18 ppm). Also, on silica TLC (3:12:2:2 chloroform/1-butanol/acetic acid/water), 4 had $R_f$ 0.43 and appeared red by ninhydrin, like the lower spot in fraction B and the middle spot in C. Palmeta and Prostenik have reported that 2-amino-3-octadecanol and 4 exhibited very similar $R_f$ values (0.32 and 0.29, respectively) when eluted on paper impregnated with silicic acid with the solvent system di-isobutyl ketone/acetic acid/water (40:25:5).

Fractions A–C were also studied by several mass spectrometric methods. The largest ion in all of the spectra was m/z 286. High resolution measurement of this peak (m/z 286.3109) allowed the assignment of the molecular formula $C_{18}H_{40}NO$ (Δ0.1 mmu) to spisulosine 285 (1). This compound derived its name, in part, from its molecular weight. This molecular formula indicated that the molecule is totally saturated. A strong peak corresponding to the loss of water from this M+H ion was observed at 268.3019 (Δ −1.5 mmu). Thus, 1 must contain a hydroxyl group. Ions corresponding to matrix adducts of m/z 286 were observed at m/z 438.3078 ($C_{22}H_{48}NO_3S_2$, Δ −0.2 mmu), 590, and 592.

One well-known primary metabolite that, like 1, consists of an 18 carbon chain substituted with hydroxyl and amine functionalities is sphingosine (4). This compound has one more oxygen and two less hydrogens than 1. The analogy appeared valid because high resolution measurement of m/z 300 for the spisulosines indicated that it was a doublet corresponding to the M+H of a higher homologue (2) of m/z 286 (300.3270, $C_{19}H_{42}NO$, Δ −0.4 mmu), together with sphingosine (4) itself (300.2914, $C_{18}H_{38}NO_2$, Δ −1.1 mmu). This also helped to explain the presence of alkene protons in the $^1$H NMR spectrum.

Several other peaks were evident in all three spectra. The ion at m/z 314 was also a doublet corresponding to $C_{20}H_{44}NO$ (314.3439, Δ −1.6 mmu), which was the molecular ion of another homologue of 1, spisulosine 313 (3), and $C_{19}H_{40}NO_2$ (314.3075, Δ −1.6 mmu) which was a homologue of sphingosine (5). Compound 4 showed matrix adducts of the M+H ion at m/z 452.2885 ($C_{22}H_{46}NO_4S_2$, Δ −1.7 mmu), 604.2831 ($C_{26}H_{54}NO_6S_4$, Δ0.3 mmu) and 606, 2995 ($C_{26}H_{56}NO_6S_4$, Δ3.6 mmu), 5 exhibited matrix adducts of the M+H ion at m/z 464.2888 ($C_{23}H_{46}NO_4S_2$, Δ −2.0 mmu) and 618.2940 ($C_{27}H_{56}NO_6S_4$, Δ5.1 mmu). It should be noted that, while m/z 300 and 314 were doublets of nearly equal intensity in fraction B, only one peak was measurable for the matrix adducts listed here from fraction B. This suggested that these two series of compounds, although very similar in general structure, behaved differently in FABMS. The spisulosine series (saturated) gave strong molecular ions and weaker matrix adducts, while the reverse was observed for the sphingosine series (unsaturated).

To better establish the structures identified by the data discussed above, several derivatives were prepared. The most informative was the diacetyl derivative of spisulosine 285 (8). Because fraction B was the largest, a portion of it was acetylated with acetic anhydride in pyridine. This mixture of acetyl derivatives will be referred to here as AcB. By silica TLC (3:12:2:2 chloroform/1-butanol/acetic acid/water), the reaction appeared quantitative, with a new spot appearing at $R_f$ 0.86. For comparison, the triacetyl derivative of authentic 4 (9) was also synthesized by the same method.

Two series of compounds related to the spisulosines have been previously isolated. Gulavita and Scheuer reported that a Xestospongia sp. sponge from Papua-New Guinea contained two epimeric 14-carbon amino alcohols 134 and 135. These were not isolated as the free amines, but rather the mixture was acetylated to give both the mono- (136, 137) and diacetyl compounds (138, 139) which were then separated. This M+H ion (m/z 370) fragmented to give m/z 310 and 268, presumably by losing acetic acid and then the second acetyl group, respectively. The comparable ions for the other spisulosines were small, but present: m/z 384, 324 and 282 for the diacetyl derivative of 2 (144), and m/z 398, 338 and 296 for the diacetyl derivative of 3 (145). The ions from the sphingosine in the sample were too small to state definitively that they were present. This again showed that the two series of compounds had very different ionization potentials. The CIMS spectrum showed strong m/z 370 and 310 ions, but here the m/z 268 ion was very, weak. The higher homologues were again seen at m/z 384 and 324 for 144, and m/z 398 and 338 for 145. Weak ions at m/z 426 and 366 were indicative of 133.

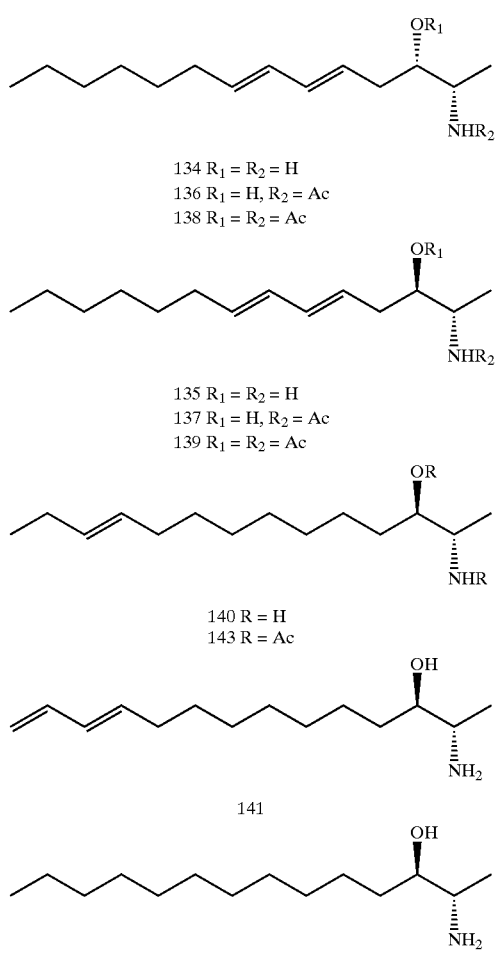

Synthesis of Spisulosine 285

To confirm the structure and determine the stereochemistry of spisulosine 285 the compound was synthesized. None of the isomers of 2-amino-3-octadecanol were previously known as natural products, but both the 2S, 3S and 2S, 3R isomers have previously been synthesized. The higher homologues are novel compounds.

A modified version of the synthesis of Prostenik and Alaupovic (Scheme IX) was used to obtain the authentic material for comparison.

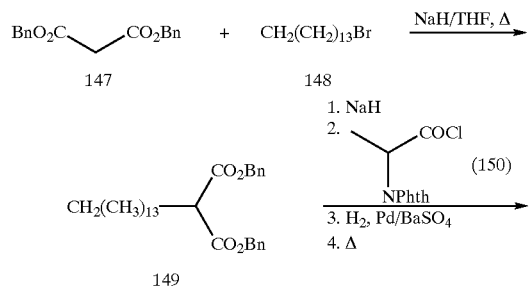

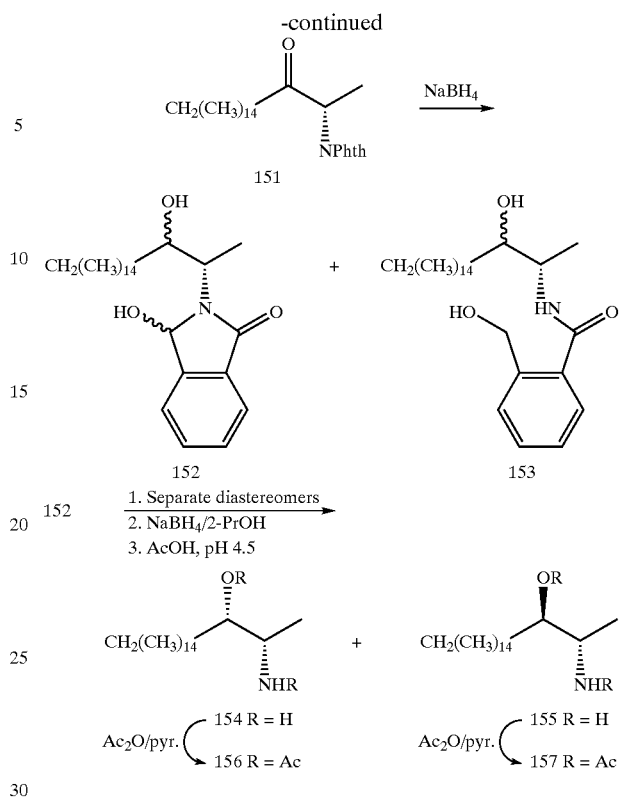

First, dibenzyl malonate (147) was alkylated with tetradecyl bromide (148). The resulting dibenzyl tetradecylamalonate (149) was then condensed with N-phthaloyl-L-alanyl chloride (150) to give 2-phthalimido-3-octadecanone (151) after removal of the benzyl groups and decarboxylation. This ketone was treated with excess sodium borohydride, which resulted in the reduction of one of the phthalimido carbonyls in addition to the ketone, producing both 152, which had one phthalimido carbonyl reduced to the carbinolamine, and 153, which was further reduced. These two products could be readily separated from each other by silica flash chromatography.

The reduction of 151 to 152 produced a mixture of four diastereomers because of the formation of two new chiral centers. At this point, the diastereomers were separated by cyano HPLC. The protecting group was then removed from each by further reduction with sodium borohydride followed by acetic acid. As one stereocentre was removed with the protecting group, this resulted in the production of two diastereomers. Since this synthesis started with L-alanine, the two products were (2S, 3S)-2-amino-3-octadecanol (154) and (2S, 3R)-2-amino-3-octadecanol (155).

Biological Activity

While the spisulosines were quite simple compounds, as illustrated in FIGS. 1A–1F, they exhibited a very unusual type of bioactivity. As discussed above, the spisulosines caused a distinct morphological change in L1210 leukemia cells, in addition to cytotoxicity. This bioactivity, which was recorded as the percentage of living cells in which altered morphology was observed, could be observed sometimes as early as 13 h after the start of the assay and reached a maximum at 50–60 h, after which it decreased. Generally 60 cells were observed to determine this number, except in assays in which less than this number of cells remained alive. The morphological effect was usually measured 30–35 h after the start of the assay and again about 24 h later, while the cytotoxicity was determined when the number of cells in the controls reached approximately 8000, usually in 3 days after the assay was begun. It should be noted that the pointed cells were live cells and that they were counted as such for the cytotoxicity reading. Also, assays in which 100% cytotoxicity was recorded may still have contained live cells (<0.5%) which may or may not have been pointed. All morphologically-changed cells were counted in the pointed cell percentage.

This change in morphology was always observed in fractions with fairly high cytotoxicity. Generally, no significant number of pointed cells were observed in assays with less than 70% growth inhibition. However, assays in which the cytotoxicity approached 100% often had lower percentages of cells with altered morphology than those with 90–98% growth inhibition. This suggested that the altered cells might be more easily killed. It is unknown whether the cytotoxicity and the morphology change resulted from the same mechanism of action. In one instance, pointed cells from an assay were recultured and found to revert to the normal state. This suggested that the effect was reversible after the compound had been metabolized. Acetylation drastically reduces the bioactivity.

To determine if the change in morphology of L1210 cells was caused by sphingosine (4) or related compounds, several authentic compounds were obtained and assayed against L1210 cells. Both sphingosine and stearylamine (131) exhibited moderate cytotoxicity, but no morphological effect. Sphingomyelins are well-known derivatives of 4 in which a phosphoryl choline unit has been added to the primary alcohol and the amine is acylated by a fatty acid. A mixture of sphingomyelins isolated from bovine brain (Sigma), which consisted mainly of stearoyl and nervonoyl sphingomyelins (161, 162), showed minimal cytotoxicity and no pointed cells. The cytotoxicity of the phosphorylcholine derivative of 4 (163, Sigma) may be, at least, partially due to hydrolysis of 163 to 4.

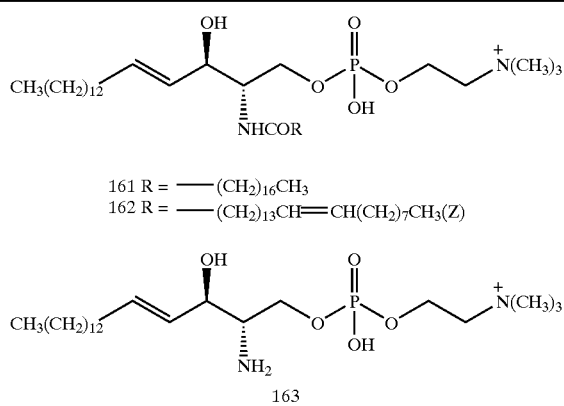

Cytotoxicity of Model Compounds

| Compound | Concentration (μg/ml) | % Inhibition | % Pointed cells |
|---|---|---|---|
| 4 | 5 | 100 | 0 |
|  | 2.5 | 100 | 0 |
|  | 1 | 75 | 0 |
|  | 0.5 | 31 | 0 |
|  | 0.25 | 13 | 0 |
|  | 0.1 | 0 | 0 |
| 161 + 162 | 50 | 7 | 0 |
|  | 25 | 0 | 0 |
|  | 10 | 0 | 0 |
| 131 | 5 | 99 | 0 |
|  | 2.5 | 96 | 0 |
|  | 1 | 19 | 0 |
|  | 0.5 | 0 | 0 |

-continued

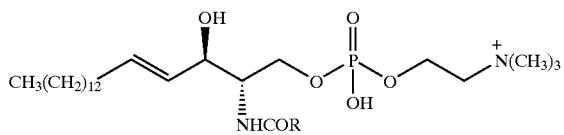

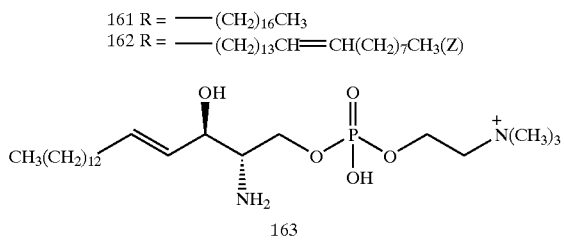

Cytotoxicity of Model Compounds

| Compound | Concentration (μg/ml) | % Inhibition | % Pointed cells |
|---|---|---|---|
| 163 | 0.25 | 0 | 0 |
|  | 0.1 | 0 | 0 |
|  | 50 | 88 | 0 |
|  | 25 | 50 | 0 |
|  | 10 | 38 | 0 |

Sphingosine and other long-chain amines, including stearylamine, are known to be cytotoxic. This bioactivity, as measured against Chinese hamster ovary (CHO) cells, has been shown to be maximal for 18-carbon homologues. All four stereoisomers of sphingosine were found to be almost equally active. Reduction of the double bond of 4 to produce dihydrosphingosine (164) did not affect the cytotoxicity. Addition of an N-methyl group to 164 also caused no significant change in the bioactivity, while acylation of the amine caused a large decrease in the cytotoxicity.

No cytotoxicity was reported for the related compounds (134, 135, 140–142) which have been isolated from other marine sources, however, they may not have been tested in this type of assay. A mixture of 134 and 135 was active against *C. albicans* (8-mm zone of inhibition for 19 mg of a mixture of the two). Xestaminol A was reported to exhibit weak activity against several Gram-positive and Gram-negative bacteria and fungi. It also showed antihelminthic activity against *Nippostrongylus brasiliensis*. Both 140 and 142 showed some activity against reverse transcriptase.

The activity of fractions A–C, the acetyl derivative of fraction B and compounds 154 and 155 is summarized in the table. The assay results clearly confirmed the NMR analysis assigning 155, not 154, as the same as 125. Also, acetylation drastically reduces the bioactivity.

TABLE IX

Bioactivity of Fractions A–C, AcB, and 154 and 155

| Sample | Concentration (μg/ml) | % Inhibition | % Pointed Cells[a/b] | |
|---|---|---|---|---|
|  |  |  | Time 1st | 2nd |
| Fraction A | 2.5 | 100 | 35,59 ad | ad |
|  | 1.25 | 100 | 25 | ad |
|  | 0.5 | 90 | 42 | 45 |
|  | 0.25 | 85 | 45 | 55 |
|  | 0.125 | 75 | 8 | 35 |
|  | 0.05 | 19 | 0 | 0 |
| Fraction B | 2.5 | 100 | 35,59 0 | 7 |
|  | 1.25 | 93 | 3 | 21 |

TABLE IX-continued

Bioactivity of Fractions A–C, AcB, and 154 and 155

| Sample | Concentration (μg/ml) | % Inhibition | % Pointed Cells[a/b] Time | 1st | 2nd |
|---|---|---|---|---|---|
|  | 0.5 | 90 |  | 2 | 43 |
|  | 0.25 | 80 |  | 7 | 37 |
|  | 0.125 | 75 |  | 5 | 21 |
|  | 0.05 | 7 |  | 0 | 0 |
| Fraction C | 2.5 | 90 | 55 | 0 |  |
|  | 1.25 | 88 |  | 0 |  |
|  | 0.5 | 63 |  | 0 |  |
| AcB | 10 | 31 | 27 | 0 |  |
|  | 5 | 38 |  | 0 |  |
|  | 2 | 13 |  | 0 |  |
|  | 1 | 0 |  | 0 |  |
|  | 0.5 | 0 |  | 0 |  |
|  | 0.2 | 0 |  | 0 |  |
| 154 | 5 | 100 | 27 | 0 |  |
|  | 2.5 | 100 |  | 0 |  |
|  | 1 | 63 |  | 0 |  |
|  | 0.5 | 0 |  | 0 |  |
|  | 0.25 | 0 |  | 0 |  |
|  | 0.1 | 0 |  | 0 |  |
| 155 | 5 | 100 | 27 | ad |  |
|  | 2.5 | 100 |  | 22 |  |
|  | 1 | 100 |  | 64 |  |
|  | 0.5 | 99 |  | 56 |  |
|  | 0.25 | 96 |  | 40 |  |
|  | 0.1 | 63 |  | 33 |  | footnote
[a]Unless otherwise indicated, the percentage of pointed cells was read twice. The number of hours after the start of the assay at which these measurements were made is indicated in the time column.
[b]ad = all dead.
[c]The percentage of growth inhibition which was recorded as the percentage of live cells in the treated wells compared to that in control wells.

Possible Mode of Action

The bioactivity of the spisulosines may be due to their similarity to sphingosine. In the nomenclature of sphingolipids, spisulosine 285 would be considered 1-deoxysphinganine. The spisulosines may compete with sphingosine for binding sites or be incorporated into sphingolipids such as sphingomyelins, ceramides or gangliosides. In either case, the spisulosines could disrupt the cellular functions controlled by these compounds. Sphingosine and its derivatives are involved in the regulation of cell growth and differentiation. Sphingosine is a potent inhibitor of protein kinase C, competing with diacylglycerol for the binding site, which may explain its cytotoxicity. Structure-activity studies have shown that this inhibition requires a positively charged amine and thus N-acyl derivatives were inactive. If the spisulosines act by competing with sphingosine, this would explain the relative lack of activity of the acetylated compounds (AcB). There is growing evidence that sphingosine may act as a second messenger by regulating protein kinase C activity. It has also been shown to inhibit the differentiation of HL-60 cells treated with phorbol 12-myristate-13-acetate, a known protein kinase C activator. The spisulosines should be tested for inhibition of protein kinase C. It is unknown whether inhibition of this enzyme could cause the morphological effects observed for the spisulosines, but protein kinase C is involved in the control of cell growth and differentiation.

Experimental

NMR spectra were obtained on General Electric GN 500 and QE 300 and Varian U400 spectrometers. Samples for NMR analysis were dissolved in $CDCl_3$ or $CD_3OD$. Chemical shifts (D) are reported in ppm downfield of tetramethylsilane (TMS) and referenced to the residual solvent peak or TMS. Low and high resolution FABMS spectra were recorded on either a VG ZAB-SE or a VG 70-SE4F spectrometer, using a 3:1 mixture of dithiothreitol-dithioerythritol (magic bullet) as the matrix. FABMS/MS spectra were recorded on a VG 70-SE4F with the same matrix, using helium as the collision gas. Cl mass spectra were recorded on a VG VSE spectrometer, operating in the alternating Cl/EI mode with methane as the reagent gas. IR spectra were obtained on an IBM IR/32 FTIR spectrometer. Optical rotations were measured on a JASCO DIP-370 digital polarimeter.

Chromatography

HPLC was carried out using an Alltech Econosphere cyano column (4.6×250 mm, 5 mm particle size). The HPLC system used consisted of a Beckman Model 114M pump, a Rheodyne 71 injector and either an Isco V^ or Beckman 165 variable wavelength detector or a Waters 990 photodiode array detector.

Analytical thin layer chromatography (TLC) was performed on a pre-coated silica gel (Merck 60 F-254) and cyano bonded-phase (EM Science CN $F_{254S}$ HPTLC) plates. Spots were visualized by UV (254 nm), ninhydrin (5% in ethanol), phosphomolybdic acid (5% in ethanol) and/or iodine. Silica column chromatography was carried out on either 50–200 mm or 40–63 mm silica gel (Merck). Other column chromatography used Chromatorex ODS (Fuji-Division 100–200 mesh) and Sephadex LH-20 (Pharmacia). High speed countercurrent chromatography (HSCCC) was performed on an Ito multi-layer coil separator-extractor (P.C., Inc.) with a #10 coil and a Milton-Roy mini-Pump. Solid phase extraction (SPE) was carried out on normal phase (silica, Alltech Maxi-Clean), reversed-phase (C-18, Waters Sep-Pak), and bonded-phase (CN, Fisher PrepSep) columns.

Biological Assays

Cytotoxicity assays against L1210 murine lymphocytic leukemia cells were performed by dissolving the samples in methanol and/or hexane were applied to the dry assay wells and the solvent was allowed to evaporate. Cells (1000) were added in minimum essential medium (MEM, 1 ml) and incubated 37° C. Inhibition of growth was recorded as the estimated percentage of living cells in sample wells versus that in control wells. This was measured when the control wells reached 8000 cells, generally three days after the start of the assay.

Morphologically-changed cells (FIGS. 1A–1F) were counted as living cells when determining the per cent inhibition of growth. Morphological changes were assessed throughout the assay period. The percentage of pointed cells was determined by counting the number of altered cells in approximately 60 living cells. This percentage varied with the length of time the assay had been running. It generally reached its maximum about 50 hours after the start of the assay, but pointed cells could be observed as early as 13 hours after the start of the assay and could usually still be seen when the percent growth inhibition was measured. The percentages of pointed cells were often counted both after about 35 and after 55 hours. The time that this measurement was made is indicated with the data.

Antimicrobial assays were performed using the filter disk diffusion method. Paper disks (6.35 or 12.7 mm, Schleicher & Schuell) were impregnated with samples (50–500 μg) in solution and allowed to dry. These disks were then placed on agar seeded with either Bacillus subtilis, Penicillium melinii (formerly P. atrovenetum), Micrococcus luteus (formerly Sarcina lutea), Escherichia coli or Saccharomyces cereuisiae. These plates were incubated for 12–24 h (32–35° C., except P. melinii, 25–27° C.).

Extraction of Spisula polynyma for Initial Biological Testing

One clam (Spisula polynyma) was thawed and the shell removed (35.32 g, wet wt). This was placed in a blender with 350 ml of 3:1 methanol/toluene and homogenized. The yellow-brown extract was filtered and added to a 1M sodium chloride solution (100 ml). The upper toluene layer was removed and the aqueous layer extracted with toluene (75 ml). The two toluene layers were combined and the solvent was removed to give a brown oily residue (333.9 mg). The aqueous layer was further extracted with dichloromethane (2×75 ml), which gave a yellow-brown residue (18.6 mg) after removal of the solvent. The aqueous layer was then extracted with ethyl acetate (75 ml). The lower phase was the organic layer due to the presence of some dichloromethane which had remained in the aqueous phase after the last step. The upper layer was further extracted with the ethyl acetate (245 ml), the upper organic layer back-extracted with water (100 ml), and the two ethyl acetate extracts were combined to give a yellow residue (36.8 mg) after removal of the solvent. The combined aqueous layers were concentrated by one-half and extracted twice with 1-butanol (150 ml, 75 ml). The combined butanol layers were back-extracted with water (75 ml), resulting in a yellow residue (132.8 mg) after removal of the butanol. The combined aqueous layers were concentrated to give an oily light yellow residue (946.1 mg). Each extract was triturated with dichloromethane and methanol to remove salts to give the toluene (302.2 mg), dichloromethane (18.6 mg), ethyl acetate (36.7 mg), butanol (120.9 mg) and aqueous (590.4 mg) extracts which were assayed.

Fractions A, B, and C

Thirty-five clams were thawed and the shells removed to give a sample of *Spisula polynyma* (1.9 kg) which was soaked in methanol/toluene (3:1, 2×1.5 l). The solids were then ground in the same solvent (6×1.5 l) and the resulting extracts filtered. A 1 M solution of sodium chloride (3 l) was added to this crude extract (12l) and the resulting upper toluene layer removed. The aqueous layer was further extracted with toluene (2×2.5l), followed by dichloromethane (4×2.5 l) as shown in FIG. 1.

After removal of the solvent, the toluene extract (21.55 g) was partitioned between methanol and hexane (1.5 l each). The methanol layer was further extracted with hexane (4×1 l). The combined hexane layers were concentrated to about 1.8 l and both extracts chilled (−10° C.). The two layers which resulted in each case were separated. The combined hexane layers were then extracted with methanol (0.5 l). This process resulted in a hexane and three methanol extracts of which the first methanol extract (6.8 g) contained the most bioactivity.

This bioactive methanol fraction was separated by flash silica chromatography employing a chloroform/methanol step gradient (100:0, 99:1, 95:5, 90:10, 85:15, 80:20, 70:30, 50:50, 0:100) to give 12 fractions. While the third, fourth, seventh and eighth fractions possessed some cytotoxicity, they showed no pointed-cell forming activity. This activity was found in the last two fractions along with most of the cytotoxicity.

These two fractions were combined (370 mg) and further purified by another flash silica column, using chloroform/1-butanol/acetic acid/water (8:12:1:1). To remove the acetic acid, each of the 12 fractions thus obtained was neutralized by (a) adding chloroform (one-quarter volume), (b) washing with 5% sodium bicarbonate until the pH of the aqueous layer was above 7 (2–3×half volume), and then (c) washing the organic layer with water (half volume). The third, and fourth and fifth fractions possessed all of the pointed cell-forming activity and essentially all of the cytotoxicity. Each of these fractions was separately purified by HPLC on a cyano column with 3:1 methanol/0.01 M ammonium formate (1 ml/min). Six fractions, of which the most bioactive was the fifth, were collected from each silica fraction. The ammonium formate was removed from each fraction by adding water (2–8 ml), applying the sample to an SPE column (C-18), washing with water (5–10 ml) and then eluting with methanol (5 ml). This resulted in fractions A (0.4 mg, $2×10^{-5}$% yield), B (1.3 mg, $7×10^{-5}$% yield) and C (0.2 mg, $1×10^{-5}$% yield), from the third, fourth and fifth silica fractions, respectively, which all eluted at t, 7.9 min.

Fraction A

White solid; silica TLC (3:12:2:2 $CHCl_3$/1-BuOH/AcOH/$H_2O$) $R_f$ 0.47 (ninhydrin-positive, pink); IR (NaCl) 2922, 2853, 1734, 1593, 1462, 1377, 1061 $cm^{-1}$; $^1H$ NMR ($CDCl_3$) d 5.38, 5.15, 3.82, 3.67, 3.44, 3.24, 2.31, 2.03, 1.67, 1.60, 1.55, 1.25, 1.10, 0.86; FABMS m/z606, 604, 592, 590, 466, 452, 438, 314, 300, 286, 268; CIMS m/z354, 340, 338, 328, 326, 324, 314, 312, 310, 300, 298, 296, 286, 284, 268, 266, 149, 139, 137,1, 123, 111, 109, 97, 95, 85, 83, 71, 69, 59, 57, 55. Anal. Calcd. For $C_{18}H_{40}NO$: 286.3110 (M+H). Found: 286.3115

Fraction B

White solid; silica TLC (3:12:2:2 $CHCl_3$/1-BuOH/AcOH/$H_2O$) $R_f$ 0.47 (ninhydrin-positive, pink), 0.44 (ninhydrin-positive, red); IR (NaCl) 3273, 2953, 2918, 2851, 1639, 1591, 1510, 1466, 1379, 1344, 1059, 970 $cm^{-1}$; $^1H$ NMR ($CDCl_3$) δ5.98, 5.78, 5.55, 5.44, 5.32, 4.43, 3.78, 3.65,3.24, 2.15, 2.08, 2.00, 1.95, 1.70, 1.44, 1.25, 1.19, 0.87; FABMS m/z6.18.2940, 616, 606.2955, 604.2831, 592, 590, 480, 466, 464.2888, 452.2885, 438, 314.3439, 314.3075, 300.3273. 300.2914, 286, 268; CIMS m/z354, 352, 342, 340, 338, 328, 326, 324, 314, 312, 310, 300, 298, 296, 286, 284, 282, 280, 268, 266, 219, 193,179, 165, 149,137,123,111,109, 97,95, 85, 83,71,69, 59, 57, 55.

Fraction C

White solid; silica TLC (3:12:2:2 $CHCl_3$/1-BuOH/AcOH/$H_2O$) $R_f$ 0.47 (ninhydrin-positive, pink), 0.44 (ninhydrin-positive, red), 0.34 (ninhydrin-positive, purple); IR (NaCl) 2924, 2853, 1593, 1456, 1352, 1063, 972 $cm^{-1}$; FABMS m/z620, 618, 616, 606, 604, 602, 466, 464, 452, 438, 314, 300, 298.2741, 296, 286, 280, 268; CIMS m/z 354, 352, 340, 338, 336, 328, 326, 324, 322, 314, 312,310, 308, 300, 298, 296, 294, 292, 286.284, 282, 280, 278, 268, 179, 165, 149, 137, 135, 1, 123, 121, 111, 109, 97, 95, 85, 83, 81, 71, 69, 60, 59, 57, 55.

Initial Partitioning

Twenty-two *S. polynyma* claims were thawed and the shells removed to give 1.3 kg of the organism (wet wt). This was placed in Waring blender with 3:1 methanol/toluene (1.5 l) and ground into a thick slurry which was filtered through a layer of celite. The solid residue was further extracted (4×1.5 l) and filtered in a similar manner. The remaining solids were then placed in 5:1 methanol/toluene (750 ml) and allowed to soak for 36 h, before filtering. To the combined filtrates (7.8 l) was added 1 M sodium chloride (2 l). After removal of the upper toluene layer, the aqueous phase was extracted with toluene (2×1.5 l) and dichloromethane (3×1.5 l). The remaining aqueous phase was concentrated by one-half and extracted with ethyl acetate (2×1 l). The resulting aqueous layer was diluted with water (2 l) and extracted twice with 1-butanol (1.5 l, 1 l). Removal of the solvents and trituration with dichloromethane and methanol resulted in the toluene (14.1 g), dichloromethane (0.75 g), ethyl acetate (1.3 g), 1-butanol (0.2 g) and aqueous (1.9 g) extracts which were assayed.

The toluene extract was partitioned between hexane and methanol (750 ml each). The resulting methanol layer was further extracted with hexane (2×750 ml, 2×500 ml). The hexane layers were combined and concentrated to about 3 l and then both extracts were chilled (−10° C.) which caused each to separate into two layers. The combined methanol layers were concentrated in vacuo to give a brown residue (methanol extract 1, 536 g). The hexane layers were further concentrated to about 1 l and back-extracted with methanol (500 ml). The solvent was removed from each of these to give the methanol extract 2 (4.26 g) and the hexane extract (4.52 g).

Fraction D

A portion of the first methanol extract (594 mg) was separated by HSCCC, using hexane/ethyl acetate/methanol/water (4:7:4:3, MP=UP) at 4 ml/min. This gave 12 fractions of which the third, fourth and fifth contained most of the bioactivity. These three fractions were combined (158 mg) and chromatographed on Sephadex LH-20, eluting with methanol. This resulted in eight fractions of which the fourth (8.4 mg) possessed the majority of the biological activity. This bioactive fraction was further purified by HPLC on a cyano column with 3:1 methanol/0.01 M ammonium formate (0.5 ml/min). Eight fractions were collected and the ammonium formate was removed from each by adding water (2–8 ml), applying the sample to an SPE column (C-18), washing with water (5–10 ml) and then eluting with methanol (5 ml). The seventh fraction ($t_r$ 15.8 min, white amorphous solid, 0.3 mg, $2 \times 10^{-4}\%$ yield) proved to contain the bioactive compounds and is referred to here as fraction D. Silica TLC (1-BuOH/AcOH/$H_2O$, 4:1:5, upper layer) showed four spots by phosphomolybdic acid visualization: $R_f$ 0.53 (major), 0.35 (major), 0.31 (minor), and 0.19 (minor). The inactive sixth fraction showed all the same spots except $R_f$ 0.53. The FABMS spectrum of fraction D showed intense peaks at m/z 286.3019, 300.3270 and 268.3019, and weaker peaks at m/z 314, 438, 452, 464, 590, 592, 669, 797, 809 and 825. The last three ions listed were also observed in most of the other HPLC fractions and appeared to correspond to the TLC spot at $R_f$ 0.35. Anal. Calcd. for $C_{18}H_{40}NO$: 286.3110 (M+H). Found: 286.3109 (HRFABMS).

Fraction E

A second portion of the first methanol extract described above (633 mg) was subjected to HSCCC. The solvent system employed was hexane/methanol/water (5:4:1, UP=MP, 5 ml/min), which gave poor stationary phase retention. This resulted in 10 fractions with the bioactivity spread throughout most of them. The first three fractions (310 mg) were combined and further purified by HSCCC using hexane/ethyl acetate/methanol/water (4:7:4:3, LP=MP, 2 ml/min) to give 12 fractions. The second to fifth fractions (85 mg), containing the majority of the bioactivity, were chromatographed on a C-18 flash column, eluting with a methanol/water/chloroform step gradient (90: 10:0, 95:5:0, 100:0:0, 95:0:5, 90:0:10, 50:0:50). This gave 10 fractions which were all bioactive.

The fourth to sixth fractions from the first HSCCC run were combined with a side fraction from the Sephadex LH-20 column discussed under fraction D (270 mg). This material was subjected to HSCCC, using the same conditions as the second run just described except that the flow rate was 3 ml/min. This resulted in nine fractions of which the second and third contained most of the cytotoxicity and cell-altering activity. These two fractions were combined (42 mg) and separated on a flash C-18 column, using a methanol/water step gradient (80:20, 90:10, 95:5, 100:0). This resulted in 12 fractions of which the eighth to eleventh showed morphology-altering activity and cytotoxicity. All but the first and fifth fractions from the first C-18 column were combined with the eighth to eleventh fractions from the second (50.4 mg) and separated by preparative silica TLC with chloroform/1-butanol/acetic acid/water (3:12:2:2). The plate was divided into eight fractions, which were scraped off and eluted with methanol. The residue from each fraction after removal of the solvent was triturated with dichloromethane and filtered. The fraction second from the top of the plate ($R_f$ 0.80–0.42) contained the bioactive material and is referred to as fraction E (5.7 mg). Analytical silica TLC of fraction E, eluting with the same solvent system, showed a single spot by ninhydrin visualization ($R_f$ 0.44), but phosphomolybdic acid spray regent showed other material which streaked throughout the middle third of the plate. The FABMS spectrum of fraction B showed m/z 286 as the major peak, with lesser peaks at m/z 268, 300, 438,452, and 592.

Fraction F

A third portion of the first methanol extract (468 mg) was separated by flash silica chromatography, using the solvent system chloroform/1-butanol/acetic acid/water (8:12:1:1). To remove the acetic acid, each of the 10 fractions thus obtained was neutralized by (a) adding water (half the volume of the fraction) and separating the two phases, (b) extracting the aqueous layer with chloroform (half volume× 2), (c) washing the combined organic layers with 5% sodium bicarbonate until the pH of the aqueous layer was above 7 (2 to 3×half volume), and then (d) washing the organic layer with water (half volume). The third fraction (24 mg), which possessed the majority of the bioactivity, was chromatographed on Sephadex LH-20, eluting with methanol, to give eight fractions. The sixth fraction (2.3 mg) was separated by repeated HPLC, using the same conditions as for the separation of fraction A–C. The ammonium formate was removed as for fraction A–C. The fraction eluting at $t_r$ 8.1 min was the most biologically active and is referred to as a fraction F. It was so small that an accurate weight could not be obtained, but probably was 100–200 μg (approximately 1 to $2 \times 10$–4% yield). The fractions eluting later than this one also showed both cytotoxic and pointed cell-forming activity, although less potent. This suggested that either the bioactive compound(s) did not elute as a well-defined peak or that different homologues eluted at different times, but were not well separated. Silica TLC (3:12:2:2 $CHCl_3$/1-BuOH/AcOH/$H_2O$) showed one ninhydrin-positive spot at $R_f$ 0.44. The later eluting fractions also showed this same spot, but less intense. The FABMS spectrum of fraction F shows (in decreasing order of intensity) m/z 286, 268, 300, 314, 344, 438, 452, 592, 669.

Dissection

A live clam was placed in a container with about 10 ml of diethyl ether and chilled (4° C.) for 20 h. It was dissected into nine organs: foot, digestive system (including the stomach, intestines and crystalline style sac), gonads, siphon, gills, heart, mantle, adductor muscles, and the remainder of the visceral mass. Each organ was first soaked in methanol toluene (3:1, 10 ml/g sample) and then homogenized in a Virtis blender. The extracts were filtered and the solvent was removed. The residue was triturated with dichloromethane and methanol to give 155 mg (foot), 60 mg (digestive system), 147 mg (gonads), 101 mg (siphon) 65 mg (gills), 2.5 mg (heart), 168 mg (mantle), 101 mg (adductor muscles) and 252 mg (visceral mass).

In a separate experiment, one foot that had been cooked was extracted in an analogous fashion (189 mg). A larger sample of cooked(l clams (483 g) was more extensively extracted by first soaking in 3:1 methanol/ toluene (3×500 ml) and then homogenizing the sample in the same solvents (5×500 ml). A small sample of the combined extracts was evaporated and redissolved in methanol for assaying.

General Procedures

Optical rotations were measured on a Jasco DIP-370 digital polarimeter, with a 3.5×50 mm 1 ml cell. Melting points were taken on a Thomas Hoover capillary melting point apparatus. $^1H$ and $^{13}C$ NMR were recorded on a Varian Unity-400 or Unity-500 spectrophotometer. Chemical shifts are reported in ppm relative to the solvent (7.26, $CDCl_3$ and 3.30, $CD_3OD$). High resolution (HRFAB) and fast atom bombardment (FAB) mass spectra were recorded on a VG ZAB-SE or a 70 SE4F mass spectrometer. TLC was done on Merck Silica Gel 60 Thin-Layer Plates. Chromatographic separations were clone by flash chromatography using 230–400 mesh Merck silica gel. All moisture sensitive reactions were run in oven-dried glassware under an atmosphere of $N_2$. Solvents were distilled prior to use: THF from benzophenone ketyl, $CH_2Cl_2$ from $CaH_2$ other solvents used were reagent grade.

(S)-2-(N,N-Dibenzylamino)propionic Acid Methyl Ester (30)

To a 300 ml round bottom was added 20 (10.0 g, 71.6 mmol), benzyl bromide (25.73 g, 150.4 mmol), $K_2CO_3$ (9.90 g, 71.6 mmol) and $CH_3CN$ (172 ml). The mixture was stirred at 60° C. until the reaction was complete by TLC. The reaction was cooler to room temperature and the solid was separated by filtration. The filtrate was concentrated in vacuo to give an oil which was purified by flash chromatography on silica gel (9:1 hexane/EtOAc) to give a colorless oil: $[\alpha]^{25}_D$=113.6 (c 1.2, $CHCl_3$); $^1$H NMR (400 MHz, $CDCl_3$) δ1.35 (d, 3H, J=7.1 Hz), 3.53 (q, 1H, J=7.0 Hz), 3.65 (d, 2H, J=1.38 Hz), 3.75 (s, 3H), 3.85 (d, 2H, J=13.8 Hz), 7.22–7.42 (m, 10H); $^{13}$C NMR (100 MHz) δ14.9, 51.1, 54.3, 56.0, 2.8, 4.1, 4.5, 139.1, 175.1; FABMS m/z 284.1 (M+H), 282.1 (M-H), 224.2 (M-COOCH$_3$); HRFABMS Calcd. for $C_{18}H_{22}NO_2$ M$_r$284.165.1 (M+H). Found M$_r$284.1650.

(S)-2-(N,N-Dibenzylamino)-1-propanol (40)

To a suspension of LiAlH$_4$ (550 mg, 14.5 mmol) in THF (20 ml) a solution of 30 (910 mg, 3.21 mmol) in THF (2 ml) was added dropwise. The solution was stirred for 15 minutes and then heated to 65° C. for 3 hours. The reaction was cooled to 0° C. and quenched with 0.1 N HCl. The reaction was filtered through Celite and the Celite washed with THF (2×15 ml) and the solvent removed in vacuo. Flash chromatography on silica gel (4:1 hexane/EtOAc, R$_f$=0.30) gave 750 mg (92% yield) of a colorless solid: mp 40–41° C. (from hexane) Literature mp 40–41° C. (from hexane) See, Stanfield et al., *J. Org. Chem.* 1981, 49, 4799–4800; $[\alpha]^{25}_D$ = +86.6 (c 1, $CHCl_3$) Literature $[\alpha]^{23}_D$ =+88.2 (c 1, $CHCl_3$) ;$^1$H NMR (500 MHz CDCl$_3$) δ0.98 (m, 3H), 2.98 (m, 1H), 3.13 (m, 1H), 3.35 (m, 3H), 3.45 (m, 1H), 3.81 (m, 2H), 7.19–7.41 (m, 10H); $^{13}$C NMR (1 MHz) δ8.6, 52.9, 54.1, 62.7, 3.2, 4.5, 5.0, 5.3; FABMS m/z 256.2 (M+H), 22 4.2 (M-CH$_2$OH); HRFABMS Calcd. for $C_{17}H_{22}NO$ M$_r$ 256.1701 (M+H). Found M$_r$ 256.1702.

(S)-2-(N,N-Dibenzylamino)propionaldehyde (50):

Dry DMSO (0.53 ml, 7.43 mmol) was added to a stirred solution of oxalyl chloride (0.31 ml, 3.6 mmol) in $CH_2Cl_2$ (7.5 ml) at −78° C. The solution was allowed to stir 15 minutes followed by the addition of 40 (740 mg, 2.90 mmol) in $CH_2Cl_2$ (7.5 ml). After 30 minutes, Et$_3$N (1.0 ml, 7.2 mmol) was added and allowed to warm to room temperature. The solution was extracted with saturated. NaHCO$_3$ (20 ml) and the aqueous layer was extracted with $CH_2Cl_2$ (2×15 ml). The organic layer was washed with saturated NaCl solution, dried with MgSO$_4$ an concentrated in vacuo at room temperature to give 720 mg (98% yield) of a yellow oil which became a solid when cooled to −20° C. The aldehyde was used without further purification. mp 52–54° C., Literature mp 55.5° C. See, Dix et al., *Arch Pharm* (*Weinheim*) 1995, 328, 203–205.; $[\alpha]^{26}_D$=−36.0 (c 1, CHCl$_3$ Literature $[\alpha]^{20}_D$=−35.1 (c 1, EtOAc); $^1$H NMR (400 MHz, CDCl$_3$) δ1.19 (d, 2H, J=7.0 Hz), 3.34 (q, 1H, J=7.0 Hz), 3.58 (d, 2H, J=13.7 Hz), 3.74 (d, 2H, J=13.7 Hz), 7.26 (m, 2H), 7.33 (m, H), 7.42 (m, 4H), 9.74 (s, 1H); $^{13}$C NMR (100 MHz) δ6.7, 54.9, 62.8, 3.3, 4.4, 4.8, 139.1, 204.6; FABMS m/z 408.2 (M+MB), 254.2 (M+H), 22.2 (M-CHO); HRFABMS Calcd. for $C_{17}H_{20}NO$ M$_r$ 254.1545 (M+H). Found M$_r$ 254.1545.

(2S,3R)-2-(N,N-Dibenzylamino)-3-octadecanol (60)

Mg ribbon (237 mg, 9.75 mmol), dibromoethane (16 μL, 0.189 mmol) in THF (160 μL) were added to a two neck flask fitted with a reflux condenser. A 2 ml of a 1-bromopentadecane solution (970 mg, 3.33 mmol, 3.25 ml THF) was added. After the reaction had started the remainder was added dropwise. To the grayish solution, 50 (105 mg, 0.413 mmol) in THF (0.5 ml) was added dropwise. The reaction was allowed to stir overnight followed by the addition of H$_2$O (5 ml) and 0.1 N HCl until the solution became clear. The mixture was extracted with EtOAc (3×10 ml). The organic layer was washed with 5% NaHCO$_3$ then saturated. NaCl solutions and dried with MgSO$_4$. The solvent was removed in vacuo to give an oil-solid mixture (750 mg). The crude material was purified by flash chromatography on silica (8:1 hexane/EtOAc, R$_f$=0.34) to give 120 mg of a solid. This solid was further purified by HPLC on silica (93:7 hexane/EtOAc) to give a colorless waxy solid (94.3 mg, 49% yield): $[\alpha]^{25}$D=+16.3 (c 1, CHCl$_3$); $^1$H NMR (500 MHz, CDCl$_3$) δ0.88 (t, 3H, J=7.0 Hz), 1.10 (d, 3H, J=6.7 Hz), 1.16–1.41 (bm, 26H), 1.56 (m, 1H), 1.69 (m, 1H), 1.79 (m, 1H), 2.72 (quin, 1H, J=6.7 Hz), 3.47 (d, 2H, J=13.8 Hz), 3.60 (m, 1H), 3.76 (d, 2H, J=13.8 Hz), 7.22 (m, 2H), 7.30 (m, 4H), 7.34 (m, 4H); $^{13}$C NMR (1 MHz) δ8.67, 14.11, 22.68, 25.90, 29.35, 29.61, 29.64, 29.68, 29.69, 31.91, 34.27, 54.79, 57.26, 73.65, 2.89, 4.25, 4.77, 140.17; FABMS m/z 465 (M+H), 448 (M-H$_2$O), 464 (M−H), 388 (M-Ph), 224 (M-C$_{16}$H$_{33}$O); HRFABMS Calcd. for $C_{32}H_{52}NO$ M$_r$ 466.4049 (M+H). Found M$_r$ 466.4037.

The assignment of the 2S,3R configuration is based on comparison of the chemical shifts of the benzyl protons in 60 to literature values for the syn and anti diastereomers of 2-(N,N-dibenzylamino)-3-pentanol. The anti isomer has a chemical shift difference of 0.29 ppm and the syn is 0.52 ppm. Comparison of other syn-anti pairs show the range for the syn isomer to be 0.44 to 0.54 ppm and the anti 0.05 to 0.29 ppm. The value for 60 is 0.29 ppm.

(2S,3R)-2-Amino-3-octadecanol (1)

To a 15 ml round bottom was added 60 (88.2 mg, 0.189 mmol) in MeOH (2 ml) and 20% Pd (OH)$_2$—C (11 mg). The mixture was stirred under 1 atmosphere of hydrogen overnight. The catalyst was removed by filtration through a 25 mm syringe filter (0.2 μm nylon membrane) and the filter was washed with 4 ml of MeOH. The solvent was then removed in vacuo to give 51.50 mg of a white solid. The product was purified by chromatography over a 6 ml LC-Si SPE tube (90:10 CH$_2$Cl$_2$/MeOH followed by 100% MeOH) to give 49.47 mg (92% yield) of a white solid: mp 66–67° C.; $[\alpha]^{26}_D$=+24.9 (c 1, CHCl$_3$); $^1$H NMR (500 MHz, CD$_3$OD) δ0.89 (t, 3H, J=7.0 Hz), 1.05 (d, 3H, J=6.6 Hz), 1.20–1.56 (bm, 31H), 2.81 (qd, 1H, J$_1$=6.6 Hz, J$_2$=3.8 Hz), 3.42 (dt, 1H, J$_1$=8.8 Hz, J$_2$=3.8 Hz); $^{13}$C NMR (1 MHz) δ14.60, 16.82, 23.90, 27.40, 30.65, 30.90, 30.95, 30.96, 33.23, 34.13, 52.33, 76.16; FABMS m/z286.3 (M+H), 268.3 (M-OH), HRFABMS Calcd. for $C_{18}H_{40}NO$ M$_r$ 286.3110 (M+H). Found M$_r$ 286.3109.

A mixture of diastereomers of 3-hydroxy-2-(1-methyl-2-2-hydroxy-heptadecyl)-isoindolin-1-one (152, 22 mg) were separated by cyano HPLC with hexane/2-propanol (98:2, 1 ml/min) to give four compounds (152a–152d). The purity of each peak was determined by reinjection on HPLC. Anal. Calcd. For $C_{26}H_{44}NO_3$: 418.3321 (M+H). Found: 418.3321 HRFABMS).

152a: 4.2 mg; t$_r$ 13.3 min; $^1$H NMR (CDCl$_3$) δ7.77 (1H, d, 7.3), 7.58 (2H, m), 7.50 (1H, m), 5.91 (2H, s), 4.51 (1H, m), 3.78 (1H, m), 1.58 (2H, m), 1.40 (3H, d, 7.1), 1.24 (26H, m), 0.87 (3H, t, 6.5); FABMS m/z 418, 400; relative ratio of diastereomers 17:1:0:0 (152a:152b:152c:152d).

152b: 13.7 mg; t$_r$ 13.9 min; $^1$H NMR (CDCl$_3$) δ7.70 (1H, d, 7.3), 7.54 (2H, m), 7.47 (1H, m), 5.88 (2H, s), 4.37 (1H, m), 3.85 (1H, m), 1.52 (2H, m), 1.27 (3H, d, 7), 1.25 (26H, m), 0.87 (3H, t, 6.5); FABMS m/z 41, 400; relative ratio of disastereomers 1:6.8:0:0 (152a:152b:152c:152d).

152c: 1.4 mg; t$_r$ 20.0 min; $^1$H NMR (CDCl$_3$) δ7.78 (1H, d, 7.3), 7.59 (2H, m), 7.51 (1H, m), 5.93 (2H, s), 4.12 (1H, m), 3.99 (1H, m), 1.58 (2H, m) 1.37 (3H, d, 7.0), 1.25 (26H, m), 0.87 (3H, t, 6.5); FABMS m/z418, 400; relative ratio of diastereomers 0:2.5:45:1(152a: 152b: 152c: 152d).

152d: 1.5 mg; t$_r$ 21.7 min; $^1$H NMR (CDCl$_3$) δ7.77 (1H, d, 7.3), 7.59 (2H, m), 7.51 (1H, m), 5.86 (2H, s), 4.12 (1H, m), 3.90 (1H, m), 1.58 (2H, m), 1.45 (3H, d, 6.6), 1.24 (26H, m), 0.87 (3H, t, 6.5); FABMS m/z 418, 400; relative ratio of diastereomers 0:1:2:21 (152a: 152b: 152c: 152d).

Each diastereomer was separately deprotected by the method of Osby et al. Each isomer was dissolved in 2-propanol/water (6:1, 0.1 M for 152a and 152b, 0.7 M for 152c and 152d). Sodium borohydride (5–10 equivalents) was added to each solution, which was then stirred at 25° C. for 24 h. Each solution was then adjusted to pH 4.5 with acetic acid and stirred at 80° C. for an additional 24 h. Ammonium formate was added to bring the pH of each solution to above 7 and then the solvent was removed from each by a stream of nitrogen. The residue from each was applied to a silica SPE column, which was first washed with hexane:2-propanol (9:1) and then the product eluted with 2-propanol. $^1$H NMR indicated that 152a and 152d produced 154 (1.15 mg, 40% and 0.48 mg, 47% respectively), while 152b and 152c produced 155 (3.35 mg, 42% and 0.38 mg, 40%, respectively).

154: White solid; silica TLC (3:12:2:2 CHCl$_3$/1-BuOH/AcOH/H$_2$O) R$_f$ 0.48 (ninhydrin-positive, pink); IR (NaCl) 2919, 2851, 1563, 1466, 1406, 758 cm$^{-1}$; FABMS m/z 438, 286, 268, 85, 70, 69, 57, 55, 44. Anal. Calcd. For C$_{18}$H$_{40}$NO: 286.3110 (M+H). Found 286.3115 (HRFABMS).

155: White solid; silica TLC (3:12:2:2 CHCl$_3$/1-BuOH/AcOH/H$_2$O) R$_f$ 0.50 (ninhydrin-positive, pink); IR (NaCl) 3281, 2917, 2849, 1568, 1520, 1470, 1412 cm$^{-1}$; FABMS m/z 438, 286, 268, 85, 70, 69, 57, 55, 44, Anal. Calcd. For C$_{18}$H$_{40}$NO: 286.3110 (M+H). Pound: 286.3109 (HRFABMS).

Acetylation

A portion of fraction B (560 μg) dissolved in acetic anhydride (200 μL) and pyridine (400 μL) and was stirred at 25° C. for 4.5 h, at which time no starting material could be observed by TLC. The solvent was 1removed by a stream of nitrogen to give AcB: off-white solid; silica TLC R$_f$ 0. 86 (3.12:2:2 CHCl$_3$/1-BuOH/AcOH/H$_2$O, phosphomolybdic acid), 0.65 (9:1 CHCl$_3$/MeOH, phosphomolybdic acid); IR (NaCl) 2922, 2853, 1741, 1651, 1547, 1460 1371, 1234, 1022, 970 cm$^{-1}$; FABMS m/z 370, 310, 268; CIMS m/z 426, 424, 412, 410, 398, 384, 370, 368, 364, 338, 324, 310, 165, 149, 139, 1, 121, 111, 97, 86, 61, 57, 55. Anal. Calcd. For C$_{22}$H$_{44}$NO$_3$: 370.3321 (M+H). Found: 370. 3326 (HRFABMS).

Triacetylsphingosine (133)

In a procedure similar to Grode and Cardellina D-erythrosphingosine (4, 2 mg, 6.7 μmol, Sigma) in acetic anhydride (1 ml) and pyridine (2 ml) was stirred at 25° C. for 4.5 h, at which time no starting material could be observed by TLC. The solvent was removed by a stream of nitrogen to give 133: white solid; silica TLC R$_f$ 0.86 (3:12:2:2 CHCl$_3$/1-BuOH/AcOH/H$_2$O, phosphomolybdic acid), 0.65 (9:1 CHCl$_3$/MeOH, phosphomolybdic acid); FABMS m/z 580, 426, 366, 306, 264; CIMS m/z 468, 454, 426, 424, 394, 366, 364, 306, 264, 144, 85, 84, 83, 61.

(2S, 3S)-2-Acetamido-3-acetoxyoctadecane (156)

(2S, 3S)-2-amino-3-octadecanol (154, 150 μg, 0.5 μmol) in acetic anhydride (50 μl) and pyridine (100 μl) was stirred at 25° C. for 5 h, at which time no starting material could be observed by TLC. The solvent was removed by a stream of nitrogen to give 156: white solid; silica TLC R$_f$ 0.86 (3:12:2:2 CHCl$_3$/1-BuOH/AcOH/H$_2$O, phosphomolybdic acid); IR (NaCl) 3286, 2924, 2853, 1740, 1653, 1541, 1456, 1371, 1238 cm$^{-1}$; FABMS m/z 522, 370, 328, 310, 286, 268. Anal. Calcd. For C$_{22}$H$_{44}$NO$_3$ 370.3321 (M+H). Found: 370.3326 (HRFABMS).

(2S, 3R)-2-Acetamido-3-acetoxyoctadecane (157)

(2S, 3R)-2-amino-3-octadecanol (155, 750 μg, 2.6 μmol) in acetic anhydride (200 μL) and pyridine (400 μL) was stirred at 25° C. for 5h, at which time no starting material could be observed by TLC. The solvent was removed by a stream of nitrogen to give 157: white solid; silica TLC R$_f$ 0.86 (3:12:2:2 CHCl$_3$/1-BuOH/AcOH/H$_2$O, phosphomolybdic acid); IR (NaCl) 3289, 2917, 2849, 1728, 1637, 1545, 1464, 1369, 1240 cm$^{-1}$; FABMS m/z 522, 370, 328, 310, 286, 268. Anal. Calcd. For C$_{22}$H$_{44}$NO$_3$: 370.3321 (M+H). Found: 370.3319 (HRFABMS).

Spisulosine 285 Acetonide (146)

A portion of fraction A (40 μg) was dissolved in acetone (200 μL) to which 0.1 N hydrochloric acid (20 μL) was added. This solution was stirred at 25° C. for 24 h, after which the solvent was removed by a stream of nitrogen. FABMS indicated that a small amount of the acetonide 146 was formed: m/z 592, 452, 438, 326.3430, 300, 286, 268. Anal. Calcd. For C$_{21}$H$_{44}$NO: 326.3423 (M+H). Found 326.3430 (HRFABMS).

(4S, 5R)-4-Methyl-5-(n-pentadecyl)-oxazolidinone (158)

(2S, 3R)-2-amino-3-octadecanol (155, 750 μg, 2.6 μmol) was dissolved in dichloromethane (100 μL) to which 1,1'-carbonyldiimidazole (0.85 mg, 5.3 μmol) and triethylamine (0.4 μL, 2.9 μmol) was added. The solution was stirred for 5 h and then the solvent removed by a stream of nitrogen. The crude product 158 was analyzed without purification: IR (NaCl) 36, 2919, 2851, 1742, 1713, 1551, 1470, 1395, 1321, 49, 1239, 1094, 1061, 1001, 768, 743, 664 cm$^{-1}$; FABMS m/z 785, 623, 474, 406, 362, 328, 312, 286, 268. Anal. Calcd. For C$_{19}$H$_{38}$NO$_2$: 312.2903 (M+H). Found: 312.2903 (HRFABMS).

Further Investigation of Changes in Cell Morphology

Materials

Lysophosphatidic acid (LPA), antibodies against tubulin and phalloidin were all obtained from Sigma. Fluorescein- and Texas red-labelled goat antimouse antibody were obtained from Amersham (U. K.). Antibody raised against the Rho protein was obtained from Sta Cruz Biotechn.

Cell Culture

Vero cells were grown in Dulbecco's modified Eagle medium supplemented with 10% foetal bovine serum. Spisulosine or LPA were added to these cultures to a concentration of 0.2–1.0 mg and 50–10 mM respectively, from 4 to 24 hours. Cells were counted with the drug exclusion haemocytometer procedure using a solution of 0.4% Trypan blue in Hanks buffered Saline (Cells and Celis, "General Procedures for Tissue Culture in Cell Biology, a Laboratory Handbook" Academic Press Inc, Vol 1, pp. 5–17.)

EXAMPLE A

Spisulosine 285 Causes Changes in Cell Morphology

Figure 3:
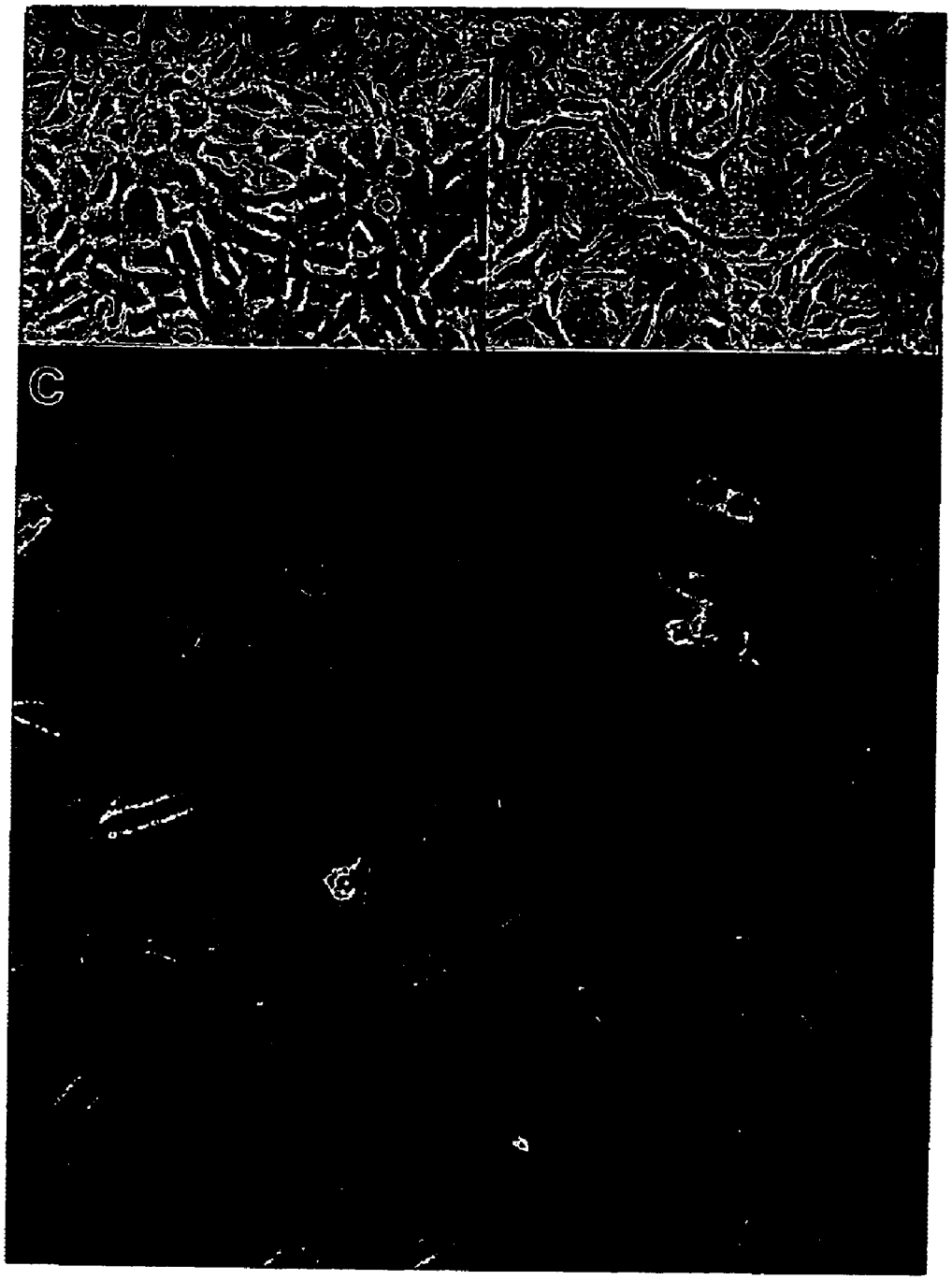
FIG. 3 is a microphotograph for the results in Example A.

Vero cells were incubated with spisulosine 285 (0.5 mM) for 4 hours. FIG. 3 is a microphotograph for the results in Example A. Cell shaped was altered from polygonal (untreated cells, panel a) to a fusiform shape (panel b). Panel c represents a higher magnification of the culture to which spisulosine was added.

EXAMPLE B

Change in Cell Morphology is Due to an Effect on the Cell Microfilaments

In order to identify the organization of the microfilament and microtubule organization in cells treated with spisulosine 285, cells were stained with phalloidin to detect actin polymers, and an antitubulin antibody to detect tubulin.

Vero cells were incubated in the presence (panel b, d) or absence (a, c) of 0.5 mM spisulosine 285 for 4 hours. Cells grown in coverslips were fixed with methanol at −20° C. (for tubulin antibody) or with 4% paraformaldehyde in phosphate buffered saline PBS (w/v) for phalloidin incubation. In the second case the cells were washed with 0.2% Triton X100 in PBS. The coverslips were washed with PBS and incubated for 1 hour at room temperature with the tubulin antibody (diluted 1/1000 in PBS) or with phalloidin (1 mg/ml). After washing with PBS the coverslips incubated with the tubulin antibody were overlaid with fluorescein or Texas red-labelled goat antimouse antibodies (diluted 1:50 in PBS). The coverslips were mounted with Mowiol and stored in the dark at 4° C. until observation.

Figure 4:
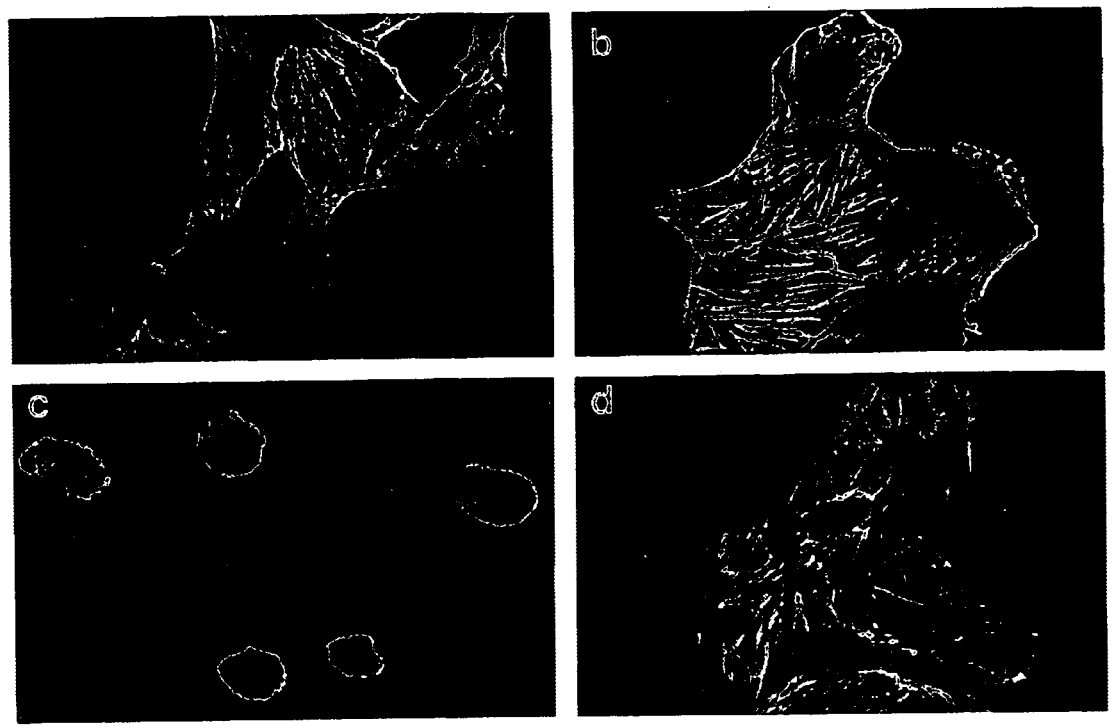
FIG. 4 is a microphotograph for the results in Example B.

FIG. 4 is a microphotograph for the results in Example B. Panel 'a' represents cells stained with phalloidin (actin stain) and not treated with spisulosine. Panel 'b' represents cells stained for phalloidin and treated with spisulosine. Panel 'c' represents cells stained for tubulin and not treated with spisulosine. Panel 'd' represents cells stained for phalloidin and treated with spisulosine. There is a dramatic decrease in actin in spisulosine-treated cells, in comparison with untreated cells. Under the same conditions, the microtubule network remains in a polymerised form.

EXAMPLE C

Effect of Spisulosine 285 on the Rho Protein

The small GTP binding protein Rho is involved in the formation of actin-myosin "stress fibers" (Hall, A., Science, 279, 1998, p 509–514). Therefore, the electrophoretic mobility and cellular distribution of Rho was analyzed in cells treated with spisulosine 285.

Figure 5:
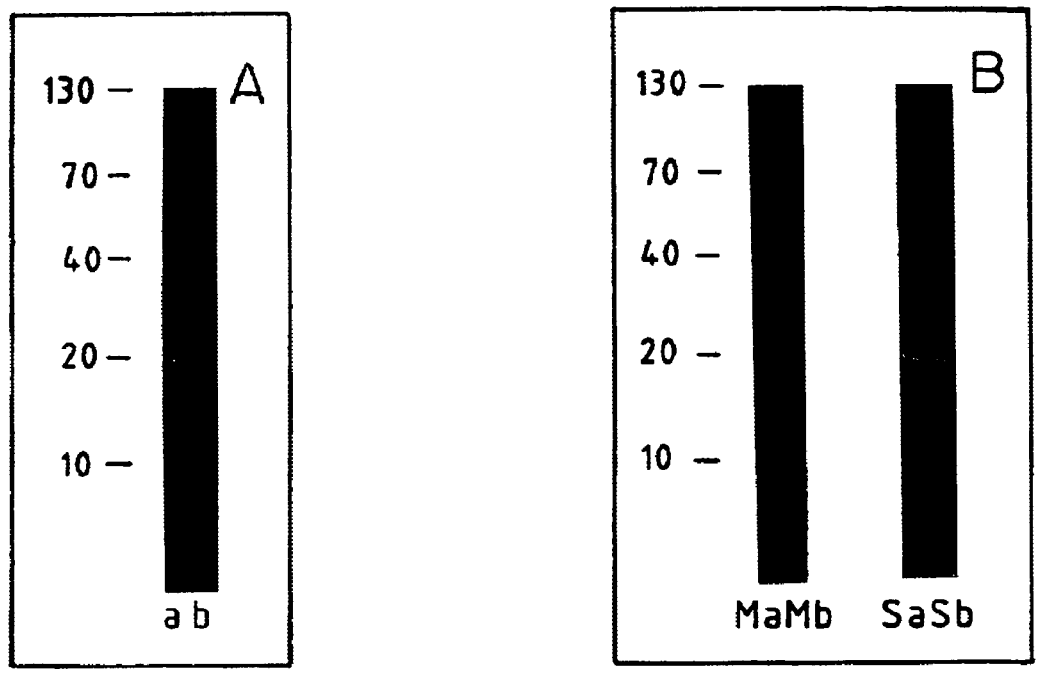
FIG. 5 is an electrophoretogram of Example C.

FIG. 5 is an electrophoretogram of Example C. In panel A, equivalent amounts of protein from a cell extract from untreated (a) or from 0.5 mM spisulosine 285 treated (20 hour) cells (b) were fractionated by gel electrophoresis and blotted onto nitrocellulose paper to analyze the amount of the Rho protein.

Subcellular fractionation was carried out by placing cells in a hypotonic buffer (0.25 M sucrose, 20 mM HEPES pH 7.4, 2 mM EDTA, 1 mM PMSF, 10 mg/ml aprotinin, leupeptine and pestatine), and lysing them with a Dounce. The homogenate was first centrifuged at 750 g for 5 minutes to remove nuclei and unbroken cells, and the supernatant was further centrifuged at 30,000 g for 1 hour (4° C.) to isolate a pelleted particulate fraction (putative membrane fraction) and a supernatant. The different fractions were characterised by electrophoresis and Western Blotting using an antibody against the Rho protein.

No significant change in the amount or mobility of Rho was observed on treatment of cells with spisulosine 285. However, a decrease in the proportion of Rho associated with the particulate fraction was observed.

EXAMPLE D

Effect of Lysophosphatidic Acid (LPA) on the Action of Spisulosine 285

LPA is known to increase the level of stress fibers in cells by activation of the Rho protein. The effect of LPA on cells treated with spisulosine 285, and untreated cells was examined.

Vero cells were incubated in the absence (a) or presence (b) of 10 mM LPA for 2 hours, or in the presence (c) of 0.5 mM spisulosine 285 for 20 hours, or in the presence (d) of first 10 mM LPA (2 hours) and afterwards with 0.5 mM spisulosine 285 for an additional 18 hours.

Figure 6:
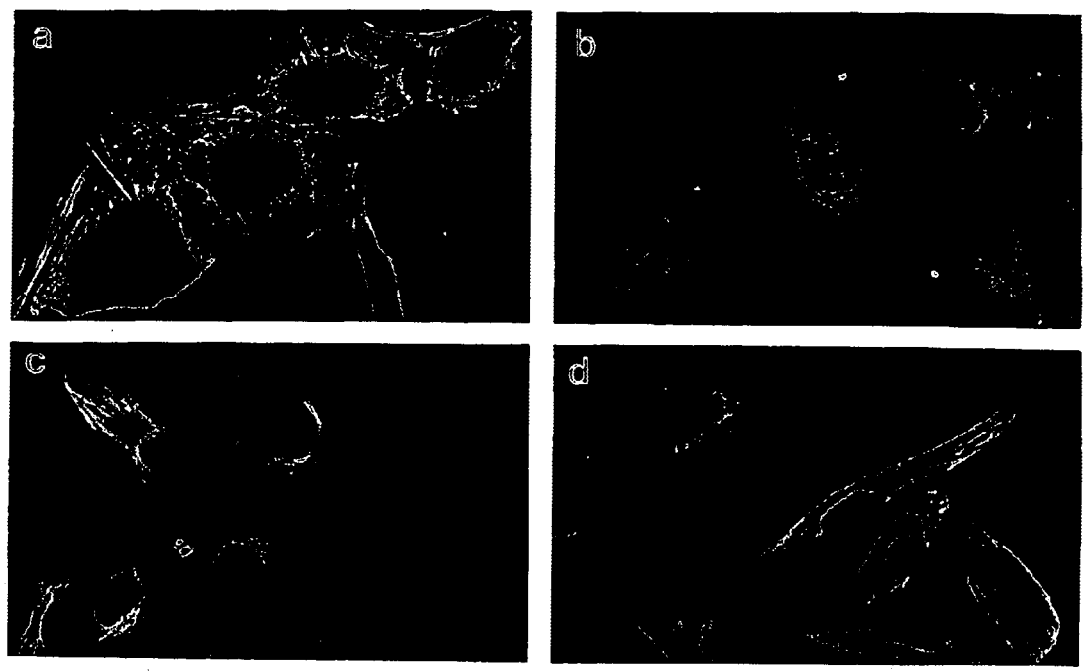
FIG. 6 is a microphotograph for the results in Example D.

FIG. 6 is a microphotograph for the results in Example D. Panel b indicates the effect of LPA in increasing the level of actin. Incubation of Vero cells with spisulosine for 24 hours results in the appearance of rounded cells, see panel c. These cells detach from the culture dish and die. The addition of LPA prior to spisulosine prevents the morphological change promoted by spisulosine.

in vivo Data

EXAMPLE E

The Effect of Spisulosine 285 in vivo

Spisulosine 285 was tested in in vivo studies against xenograft models of human prostate cancer (PC-3) and human renal cancer (MRI-H-121). These models use subcutaneously implanted solid human tumours that grow and increase in volume over time. The mean volume of tumour growth in control animals provides the basis for comparison. For active compounds the tumour growth is inhibited either completely (%T/C values<1%, or negative), or partially (>1% T/C–50% T/C). A level of activity that is less than 40% T/C is considered statistically significant. The doses of spisulosine used were given at the maximum tolerated, non lethal dose (MTD), ½ MTD and ¼ MTD. Delivery of the drug was by the intraperitoneal route.

| Compound | Total Dose (mg/kg) | % T/C | Day | Comments |
|---|---|---|---|---|
| Human prostate cancer PC-3 | | | | |
| Spisulosine 285 | 9.990 | −21% | 11 | stasis (complete remission) |
| Spisulosine 285 | 5.010 | −1% | 11 | stasis (complete remission) |
| Spisulosine 285 | 2.499 | 223% | 15 | |
| Control | | 100% | 15 | |
| Human MRI-H-121 renal cancer | | | | |
| Spisulosine 285 | 9.990 | 28% | 11 | inhibition (partial remission) |
| Spisulosine 285 | 5.010 | 35% | 11 | inhibition (partial remission) |
| Spisulosine 285 | 2.499 | 43% | 15 | |
| Control | | 100% | 15 | |

Spisulosine 285 is effective against both tumour types, significantly reducing the tumour size in the case of the human prostate cancer model PC-3 at higher doses. Spisulosine 285 reduces the growth of the human renal cancer, with effects continuing up to a few weeks after the last dose of the drug.

EXAMPLE F

An expanded in vitro screen was performed of spisulosine 285 against a series of different cell lines. The following data was obtained:

| Category | Line | Tumour | IC50 | CV-1 Therapeutic Index |
|---|---|---|---|---|
| Solid | SK-HEP-1 | Liver | 3.51 E-15 | 7863 |
| | PANC-1 | Pancreas | 1.71 E-12 | 16 |
| | HT-29 | Colon | 2.56 E-12 | 11 |
| | 786-0 | Renal | 2.75 E-12 | 10 |
| | FADU | Pharnynx | 4.99 E-12 | 6 |
| | Hs 746T | Stomach | 7.89 E-12 | 3 |
| | SK-OV-3 | Ovary | 1.40 E-11 | 2 |
| | MX-1 | Mammary | 3.89 E-11 | 1 |
| | RAMOS | Burkitts | 4.82 E-11 | 1 |
| | P3HR1 | Burkitts | 6.73 E-11 | 0 |
| | SW684 | Fibrosarcoma | 1.05 E-09 | 0 |
| Lymphoma | U-937 | Lymphoma | 1.96 E-11 | 1 |
| | H9 | Lymphoma | 3.10 E-11 | 1 |

-continued

| Category | Line | Tumour | IC50 | CV-1 Therapeutic Index |
|---|---|---|---|---|
| Leukemia | HL60 | Leukemia | 8.50 E-12 | 3 |
| | ARH77 | Leukemia | 1.36 E-12 | 2 |
| | K562 | Leukemia | 1.57 E-11 | 2 |
| | CCRF-SB | Leukemia | 1.05 E-09 | 0 |
| Normal | CV-1 | Kidney fibroblasts | 2.76 E-11 | 1 |

The range of $IC_{50}$ potencies against the tumour cell lines are from nanomolar, 1.05 E–09 nM, to femtomolar, 3.51 E–15 mM. It is exceptional to go beyond the nM and pM range to find a drug which has activity in the mM range.

The activities against the solid tumours were generally 1 log more potent than against the leukemias and lymphomas. Among the solid tumours, the most slow growing were the most sensitive, culminating with the very slow growing hepatoma SK-HEP-1.

The best therapeutic indices compared to the CV-1 normal cell line were seen with the slow growing solid tumours, since the $IC_{50}$ potency (2.76 E-11) was comparable to the leukemia/lymphomas. The solid tumour TIs ranged from 1–20 units and the TI for the hepatoma was >3 log.

The renal tumour cell line was in the most active group, pM potencies, which correlates well to the in vivo xenograft data.

REFERENCES

The following references provide background information related to the present invention. The disclosures of each are hereby incorporated herein by reference.

Vaught, K. C. A. *Classification of the Living Mollusca;* Abbott, R. T.; Boss, K. J., Eds.; American Malacologists: Melbourne, Fla. 1989; pp. 113–6.

Brusca, R. C.; Brusca, G. J. *Invertebrates;* Sinauer Associates: Sunderland, Ma., 1990; pp. 706–709.

Barnes, R. D. *Invertebrate Zoology;* 4th ed.; Saunders College: Philadelphia, 1980; p 425.

Engemann, J. G.; Hegner, R. W. *Invertebrate Zoology;* 3nd ed.; Macmillan: New York, 1981; pp. 454–467.

Palameta, B.; Prostenik, :M. *Croat. Chem. Acta* 1961, 33, 133–135.

Kawano, Y.; Highchi, R.; Isobe, R.; Komori, T. *Liebigs Ann. Chem.* 1988, 19–24.

Gulavita, N. K.; Scheuer, P. J. *J. Org. Chem.* 1989, 54, 366–369.

Jimenez, C.; Crews, P. *J. Nat. Prod.* 1990, 53, 978–982.

Mori, K.; Matsuda, H. *Liebigs Ann. Chem.* 1992, 131–137.

Prostenik, M.; Alaupovic, P. *Croat. Chem. Acta* 1957, 29, 393–402.

Osby, J. O.; Martin, M. G.; Ganem, B. *Tetrahedron Lett.* 1984, 25, 2093–2096.

Stoffel, W. *Ann. Rev. Biochem.* 1971, 40, 57–82.

Merrill, A. H., Jr.; Nimkar, S.; Menaldino, D.; Hannun, Y. A.; Loomis, C.; Bell, R. M., Tyagi, S. R.; Lambeth, J. D.; Stevens, V. L.; Hunter, R.; Liotta, D. C. *Biochemistry* 1989, 28, 3138–3145.

Hannun, Y. A.; Bell, R. B. *Science* 1989, 243, 500–507.

Merrill, A. H., Jr. *J. Bioenerg. Biomem.* 1991, 23, 83–104.

Witten, J. L.; Schaffer, M. H.; O'Shea, M.; Cook, J. C.; Hemling, M. E.; Rinehart, K. L., Jr. *Biochem. Biophys. Res. Commun.* 1984, 124, 350–358.

Shaw, P. D.; McClure, W. D.; Van Blaricom, F.; Sims, J.; Fenical, W.; Rude, J. In *Food and Drugs from the Sea* 1974; Webber, H. H.; Ruggieri, G. D., Eds.; Marine Technological Society: Washington, D.C., 1976; pp. 429–433.

Herrmann, E. C., Jr. *Progr. Med. Virol.* 1961, 3, 158–192.

Grode, S. H.; Cardellina, J. H., II *Lipids,* 1983, 18, 889–893.

Mackay and Hall, *J. Biol. Chem.,* 273, 20685–20688, 1998).

Hall, A., *Science* 279, 509–514, 1998

Itoh, et al., *Nature Medicine,* Vol 5, No. 2, 1999

Celis and Celis, *General Procedures for Tissue Culture in Cell Biology, a Laboratory Handbook* Academic Press Inc, Vol 1, pp. 5–17.)

The present invention has been described in detail, including the preferred embodiments thereof. However, it will be appreciated that those skilled in the art, upon consideration of the present disclosure, may make modifications and/or improvements on this invention.

This invention was made with Government support under Contract Number AI-04769 awarded by the Naional Institutes of Health (NIH). The Government has certain rights in the invention.

What is claimed is:

1. A method of treating one or more tumors in a mammal wherein said method comprises administering to a mammal in need of such treatment an effective antitumor amount of a pharmaceutical composition comprising a spisulosine compound having a straight chain alkane group of 16 to 24 carbon atoms, substituted with a 2-amino group and a 3-hydroxy group, and wherein one or more said tumors are selected from the group consisting of breast, head and neck, prostate, bladder, pancreas, lung, esophagus, larynx, liver, colon, thyroid, melanoma, kidney, testicular, ovarian, gastrointestinal, hepatocellular carcinoma, vascular endothelial, and endocrine gland cancer.

2. The method according to claim 1, wherein said one or more tumors are liver tumors.

3. The method according to claim 2, wehrein said one or more liver tumors are hepatoma.

4. The method according to claim 1, wherein the spisulosine compound has 18 carbon atoms.

5. The method according to claim 1, wherein the spisulosine compound has 19 carbon atoms.

6. The method according to claim 1, wherein the spisulosine compound has 20 carbon atoms.

7. The method according to claim 1, wherein the spisulosine compound is (S)-2-amino-(R)-3-hydroxy-octadecane.

8. The method according to claim 1, wherein the spisulosine compound is (S)-2-amino-(R)-3-hydroxy-nonadecane.

9. The method according to claim 1, wherein the spisulosine compound is (S)-2-amino-(R)-3-hydroxy-eicosane.

* * * * *